US009566325B2

(12) United States Patent
Yang et al.

(10) Patent No.: US 9,566,325 B2
(45) Date of Patent: Feb. 14, 2017

(54) THERAPEUTIC VACCINES FOR TREATING HERPES SIMPLEX VIRUS TYPE-2 INFECTIONS

(71) Applicant: BIOMEDICAL RESEARCH MODELS, INC., Worcester, MA (US)

(72) Inventors: Kejian Yang, Worcester, MA (US); Dennis L. Guberski, Worcester, MA (US)

(73) Assignee: BIOMEDICAL RESEARCH MODELS, INC., Worcester, MA (US)

( * ) Notice: Subject to any disclaimer, the term of this patent is extended or adjusted under 35 U.S.C. 154(b) by 0 days.

(21) Appl. No.: 14/149,670

(22) Filed: Jan. 7, 2014

(65) Prior Publication Data
US 2014/0193483 A1 Jul. 10, 2014

Related U.S. Application Data

(60) Provisional application No. 61/799,552, filed on Mar. 15, 2013, provisional application No. 61/749,682, filed on Jan. 7, 2013.

(51) Int. Cl.
*A61K 39/12* (2006.01)
*A61K 39/00* (2006.01)
*A61K 39/245* (2006.01)
*C07K 16/08* (2006.01)
*C07K 14/03* (2006.01)
*C07K 14/035* (2006.01)
*A61K 38/00* (2006.01)
*C07K 14/005* (2006.01)

(52) U.S. Cl.
CPC ............ *A61K 39/12* (2013.01); *A61K 38/00* (2013.01); *A61K 39/245* (2013.01); *A61K 2039/543* (2013.01); *A61K 2039/55555* (2013.01); *C07K 14/005* (2013.01); *C07K 14/03* (2013.01); *C07K 14/035* (2013.01); *C07K 16/085* (2013.01); *C12N 2710/16634* (2013.01)

(58) Field of Classification Search
CPC ...... A61K 39/12; A61K 38/00; A61K 39/245; A61K 2039/53; A61K 39/39; A61K 2039/545; A61K 9/0019; A61K 31/713; A61K 38/10; A61K 2039/525; A61K 2039/55566; A61K 2039/55572; A61K 2039/57; A61K 39/42; A61K 2039/5252; A61K 2039/5258; A61K 2039/54; A61K 2039/543; A61K 9/006; A61K 2039/541; A61K 2039/55555; A61K 2039/55577; A61K 35/76; A61K 38/162; C07K 14/005; C07K 14/035; C07K 16/085; C12N 7/00; C12N 15/86; C12N 2710/16634; C12N 15/1133
See application file for complete search history.

(56) References Cited

U.S. PATENT DOCUMENTS

| | | | |
|---|---|---|---|
| 5,013,556 A | 5/1991 | Woodle et al. | |
| 5,171,568 A | 12/1992 | Burke et al. | |
| 5,213,804 A | 5/1993 | Martin et al. | |
| 5,225,212 A | 7/1993 | Martin et al. | |
| 5,290,563 A | 3/1994 | Millet-Genin et al. | |
| 5,356,633 A | 10/1994 | Woodle et al. | |
| 5,540,935 A | 7/1996 | Miyazaki et al. | |
| 5,543,152 A | 8/1996 | Webb et al. | |
| 5,556,948 A | 9/1996 | Tagawa et al. | |
| 5,612,041 A | 3/1997 | Burke et al. | |
| 5,747,039 A | 5/1998 | Burke et al. | |
| 6,027,730 A | 2/2000 | Francotte et al. | |
| 6,451,320 B1 | 9/2002 | Stephenne et al. | |
| 6,641,818 B1 | 11/2003 | Spear et al. | |
| 6,692,752 B1 | 2/2004 | Slaoui et al. | |
| 2003/0008000 A1 | 1/2003 | Wong et al. | |
| 2003/0072794 A1* | 4/2003 | Boulikas ....................... 424/450 |
| 2004/0151734 A1 | 8/2004 | Slaoui et al. | |
| 2006/0035853 A1* | 2/2006 | Yang et al. ..................... 514/44 |
| 2006/0110736 A1 | 5/2006 | Donnelly et al. | |
| 2006/0257426 A1* | 11/2006 | Baker et al. ............... 424/204.1 |
| 2008/0102087 A1 | 5/2008 | Vilalta et al. | |
| 2009/0246227 A1 | 10/2009 | Friedman et al. | |
| 2011/0177125 A1 | 7/2011 | Friedman et al. | |

(Continued)

FOREIGN PATENT DOCUMENTS

WO  WO 00/11140       3/2000
WO  WO 0076476 A1 * 12/2000
(Continued)

OTHER PUBLICATIONS

Halford WP. Antigenic breadth: a missing ingredient in HSV-2 subunit vaccines? Expert Rev Vaccines. Jun. 2014;13(6):691-710.*
Williams JA, Luke J, Johnson L, Hodgson C. pDNAVACCultra vector family: high throughput intracellular targeting DNA vaccine plasmids. Vaccine. May 22, 2006;24(21):4671-6. Epub Aug. 26, 2005.*
Abdulhaqq SA, Weiner DB. DNA vaccines: developing new strategies to enhance immune responses. Immunol Res. 2008;42(1-3):219-32.*
Dolan A. envelope glycoprotein D [Human herpesvirus 2]. NCBI Acc. No. NP_044536.1. Dep. Apr. 3, 2000.*
Takasaki J, Ansell SM. Micelles as intermediates in the preparation of protein-liposome conjugates. Bioconjug Chem. Mar.-Apr. 2006;17(2):438-50.*
van Kooij A, Middel J, Jakab F, Elfferich P, Koedijk DG, Feijlbrief M, Scheffer AJ, Degener JE, The TH, Scheek RM, Welling GW, Welling-Wester S. High level expression and secretion of truncated forms of herpes simplex virus type 1 and type 2 glycoprotein D by the methylotrophic yeast Pichia pastoris. Protein Expr Purif. Aug. 2002;25(3):400-8.*

(Continued)

Primary Examiner — Rachel B Gill
(74) Attorney, Agent, or Firm — Cooley, LLP

(57) ABSTRACT

The invention provides methods and kits for inducing a therapeutic immunity in animals (e.g. mammals) against viral antigens, including herpes-simplex virus type 2. In particular, the invention provides a method of treating animals with an established HSV-2 infection by administering a therapeutic vaccine comprising a priming dose of a nucleic acid encoding an HSV-2 antigen, an initial or first boosting dose comprising the protein form of the antigen encapsulated in liposomes, and one or more subsequent boosting doses comprising both the nucleic acid encoding the HSV-2 antigen and the liposomal-encapsulated protein antigen.

24 Claims, 7 Drawing Sheets

(56) References Cited

U.S. PATENT DOCUMENTS

| | | | |
|---|---|---|---|
| 2012/0027841 A1* | 2/2012 | Yang et al. | 424/450 |
| 2012/0141526 A1* | 6/2012 | Baker et al. | 424/208.1 |
| 2012/0308598 A1 | 12/2012 | Mueller et al. | |
| 2012/0328658 A1 | 12/2012 | Vilalta et al. | |
| 2013/0195961 A1* | 8/2013 | Yang et al. | 424/450 |

FOREIGN PATENT DOCUMENTS

| | | | |
|---|---|---|---|
| WO | WO 01/44477 | 6/2001 | |
| WO | WO 2011112717 A1 * | 9/2011 | A61K 9/127 |

OTHER PUBLICATIONS

Strasser JE, Arnold RL, Pachuk C, Higgins TJ, Bernstein DI. Herpes simplex virus DNA vaccine efficacy: effect of glycoprotein D plasmid constructs. J Infect Dis. Nov. 2000;182(5):1304-10. Epub Oct. 4, 2000.*

Tirabassi RS, et. al. Vaccine. Jan. 29, 2011;29(5):1090-8. Epub Dec. 4, 2010.*

Soleimanjahi H, Roostaee MH, Rasaee MJ, Mahboudi F, Kazemnejad A, Bamdad T, Zandi K. The effect of DNA priming-protein boosting on enhancing humoral immunity and protecting mice against lethal HSV infections. FEMS Immunol Med Microbiol. Feb. 2006;46(1):100-6.*

Vollbach, European Supplementary Search Report for EP Application No. 11754011.2, mailed Jul. 18, 2013 (5 pages).

Tirabassi et al., "A Mucosal Vaccination Approach for Herpes Simplex Virus Type-2," Vaccine, vol. 29: 1090-1098, 2011.

EO et al., Prime-Boost Immunization with DNA Vaccine: Mucosal Route of Administration Changes the Rules, Journal of Immunology, vol. 166: 5473-5479, 2001.

Zhou et al., "Humoral Immunization and Cell-Mediated Immunization Evoked by HBsAg and B7-2 Ag Coexpression Recombinant Adenovirus Vector," Zhonghua Gan Zang Bing Za Zhi, vol. 9: 111-113, Abstract, Apr. 2001.

Childers et al., "Nasal Immunization of Humans with Dehydrated Liposomes Containing *Streptococcus mutans* Antigen," Oral Microbiol. Immunol., vol. 12: 329-335, 1997.

Childers et al., "A Controlled Clinical Study of the Effect of Nasal Immunization with a *Streptococcus mutans* Antigen Alone or Incorporated into Liposomes on Induction of Immune Responses," Infection and Immunity, vol. 67: 618-623, 1999.

Almeida et al., "Nasal Delivery of Vaccines," Journal of Drug Targeting, vol. 3: 455-467, 1996.

Manosroi, A. et al., "Characterization of Amphotericin B Liposome Formulations," Drug Development and Industrial Pharmacy, vol. 30(5), Abstract, 2004.

Weisiger, R., "Saturable Stimulation of Fatty Acid Transport Through Model Cytoplasm by Soluble Binding Protein," American Journal Physiology Gastrointestinal and Liver Physiology, vol. 277:G109-G119, 1999.

Childers, N. et al., "Adjuvant Activity of Monophosphoryl Lipid A for Nasal and Oral Immunization with Soluble or Liposome-Associated Antigen," Infection and Immunity, vol. 68(10):5509-5516, 2000.

Aramaki Y. et al., "Activation of Systemic and Mucosal Immune Response Following Nasal Administration of Liposomes," Vaccine, vol. 12(13): 1241-1245, 1994.

Partidos, C.D. et al., "Mucosal Immunization with a Measles Virus CTL Epitope Encapsulated in Biodegradable PLG Microparticles," Journal of Immunological Methods, vol. 195:135-138, 1996.

Mora A. L. et al., "Controlled Lipidation and Encapsulation of Peptides as a Useful Approach to Mucosal Immunizations," The Journal of Immunology, vol. 161:3616-3623, 1998.

Kunisawa J. et al., "Sendai Virus Fusion Protein-Mediates Simultaneous Induction of MHC Class I/II-Dependent Mucosal and Systemic Immune Responses Via the Nasopharyngeal-Associated Lymphoreticular Tissue Immune System," The Journal of Immunology, vol. 167:1406-1412, 2001.

Fujii et al., "Enhancement of Systemic and Mucosal Immune Responses Following Oral Administration of Liposomes," Immunology Letters, vol. 36:65-70, 1993.

Babai et al., "A Novel Influenza Subunit Vaccine Composed of Liposome-Encapsulated Hemagglutinin/Neuraminidase and IL-2 or GM-CSF. I. Vaccine Characterization and Efficacy Studies in Mice," Vaccine, vol. 17: 1223-1238, 1999.

Abraham et al., "Intranasal Immunization with Liposomes Containing IL-2 Enhances Bacterial Polysaccharide Antigen-Specific Pulmonary Secretory Antibody Response," J Immunol, vol. 149: 3719-3726, 1992.

Davis et al., "DNA-mediated immunization to hepatitis B surface antigen: longevity of primary response and effect of boost," Vaccine, vol. 14(9):910-915, 1996.

Dong-Ji et al., "Priming with Chlamydia trachomatis Major Outer Membrane Protein (MOMP) DNA followed by MOMP ISCOM Boosting Enhances Protection and Is Associated with Increased Immunoglobulin A and Th1 Cellular Immune Responses," Infection and Immunity, vol. 68(6):3074-3078, 2000.

Richmond et al., "Studies of the Neutralizing Activity and Avidity of Anti-Human Immunodeficiency Virus Type I Env Antibody Elicited by DNA Priming and Protein Boosting," Journal of Virology, vol. 72(11):9092-9100, 1998.

Sin et al., "DNA Priming-Protein Boosting Enhances Both Antigen-Specific Antibody and Th1-type Cellular Immune Responses in a Murine Herpes Simplex Virus-2 gD Vaccine Model," DNA and Cell Biology, vol. 18(10):771-779, 1999.

Yasutomi et al., "A Vaccine-Elicited, Single Viral Epitope-Specific Cytotoxic T Lymphocyte Reponse Does Not Protect against Intravenous, Cell-Free Simian Immunodeficiency Virus Challenge," J Virol, vol. 69: 2279-2284, 1995.

Michel et al., "Immunotherapy of Chronic Hepatitis B by Anti HBV Vaccine: From Present to Future," Vaccine, vol. 19:2395-2399, 2001.

Tanghe et al., "Improved Immunogenicity and Protective Efficacy of a Tuberculosis DNA Vaccine Encoding Ag85 by Protein Boosting," Infection and Immunity, vol. 69: 3041-3047, 2001.

Da'Dara et al., "A DNA-prime/protein-boost vaccination regimen enhances Th2 immune responses but not protection following *Schistosoma mansoni* infection," Parasite Immunology, vol. 25: 429-437, 2003.

Haddad et al., "Characterization of Antibody Responses to a *Plasmodium falciparum* Blood-Stage Antigen Induced by a DNA Prime/Protein Boost Immunization Protocol," Scand J Immunol, vol. 49: 506-514, 1999.

Martinez et al., "Combining DNA and protein vaccines for early life immunization against respiratory syncytial virus in mice," Eur. J. Immunol, vol. 29: 3390-3400, 1999.

Zhou et al., "Reciprocal priming-boosting role of HbsAg and DNA vaccines," Zhonghua Gan Zang Bing Za Zhi, vol. 11:212-214, Abstract, Apr. 2003.

Brunel et al., "Cationic lipid DC-Chol induces an improved and balanced immunity able to overcome the unresponsiveness to the hepatitis B vaccine," Vaccine, vol. 17: 2192-2203, 1999.

Law et al., "Characterization of calcitonin-containing liposome formulations for intranasal delivery," J. Microencapsulation, vol. 18: 211-221, 2001.

De Haan et al, "Mucosal immunoadjuvant activity of liposomes: induction of systemic IgG and secretory IgA responses in mice by intranasal immunization with an influenza subunit vaccine and coadministered liposomes," Vaccine, vol. 13: 155-162, 1995.

Aramaki Y. et al., "Interferon-γ inductive effect of liposomes as an immunoadjuvant," Vaccine, vol. 13: 1809-1814, 1995.

Stanberry, "Clinical Trials of Prophylactic and Therapeutic Herpes Simplex Virus Vaccines," Herpes, vol. 11, Supplement 3: 161A-169A-, 2004.

Lasky et al., "Uniprot Accession P03172," http://www.uniprot.org/uniprot/P03172.txt?version=56, 2009.

Chu et al., "Antibody-mediated protection against genital herpes simplex virus type 2 disease in mice by Fc gamma receptor-dependent and -independent mechanisms," J. Reprod. Immunol., vol. 78: 58-67, 2008.

(56) References Cited

OTHER PUBLICATIONS

Young, International Search Report and Written Opinion for International Application No. PCT/US2011/027751, mailed Jul. 7, 2011 (13 pages).

Szoka et al., "Preparation of unilamellar liposomes of intermediate size (0.1-0.2 mumol) by a combination of reverse phase evaporation and extrusion through polycarbonate membranes." Biochim Biophys Acta., vol. 601 (3):559-71, 1980.

Ott et al.,"The Use of Muramyl Peptides as Vaccine Adjuvants." In: "Vaccine Research and Developments." Koff WC and Six HR, eds. Chapter 4: pp. 89-114, 1992.

Dutton et al., "A Novel DNA Vaccine Technology Conveying Protection against a Lethal Herpes Simplex Viral Challenge in Mice." PLoS One, vol. 8(10):e76407, 2013.

Watson. NCBI GenBank Dep. No. AAA45841. Dep. Aug. 2, 1993.

Beckman-Coulter. "Codon-optimization to PCR," Nature, vol. 425(6957):540, 2003.

Swenson et al., "Pharmacokinetics and in vivo activity of liposome encapsulated gentamicin," Antimicrob Agents Chemother., vol. 34(2):235-40, 1990.

Perrie, "Liposome-entrapped plasmid DNA: characterisation studies," Biochim Biophys Acta., vol. 1475(2):125-32, 2000.

Johnston, "Current status and prospects for development of an HSV vaccine," Vaccine, Sep. 6, 2013. pii:S0264-41 OX(13)01178-X. doi: 10.1 016/j.vaccine.2013.08.066.).

Van Lint, et al. "Herpes Simplex Virus-Specific CD8+ T Cells Can Clear Established Lytic Infections from Skin and Nerves and Can Partially Limit the Early Spread of Virus after Cutaneous Inoculation", J Immunol, 2004, pp. 392-397, vol. 172.

Kirman, et al., "DNA vaccination: the answer to stable, protective T-cell memory?" Current Opinion in Immunology, 2003, pp. 471-476, vol. 15.

Woodland, "Jump-starting the immune system: prime-boosting comes of age", Trends in Immunology, Feb. 2004, pp. 98-104, vol. 25, No. 2.

Meseda, et al., "Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone", The Journal of Infectious Diseases, 2002, pp. 1065-1073, vol. 186.

Yang, et al. "A DNA Vaccine Prime Followed by a Lipsome-Encapsulated Protein Boost Confers Enhanced Mucosal Immune Responses and Protection", The Journal of Immunology, 2008, pp. 6159-6167, vol. 180.

Morello et al., "Immunization with Herpes Simplex Virus 2 (HSV-2) Genes plus Inactivated HSV-2 Is Highly Protective against Acute and Recurrent HSV-2 Disease", Journal of Virology, 2011, pp. 3461-3472, vol. 85, No. 7.

\* cited by examiner

SEQUENCE LISTING

<160> NUMBER OF SEQ ID NOS: 7

<210> SEQ ID NO 1
<211> LENGTH: 1179
<212> TYPE: DNA
<213> ORGANISM: Artificial Sequence
<220> FEATURE:
<223> OTHER INFORMATION: Human codon-optimized HSV-2 gD nucleotide
      sequence

<400> SEQUENCE: 1
atgggacggc tgaccagcgg agtgggcaca gccgccctgc tggtcgtggc cgtgggcctg      60

```
cgcgtggtgt gcgccaagta cgccctggcc gaccccagcc tgaagatggc cgaccccaac    120
cggttccgcg gcaagaacct gcccgtgctg accagctga ccgaccctcc cggcgtgaag     180
cgcgtgtacc acatccagcc cagcctggag gacccttcc agcccccag catcccatc      240 accgtgtact acgccgtgct ggagcgcgcc tgccggagcg tgctgctgca cgcccccagc    300 gaggccccc agattgtgcg cggagccagc gacgaggccc ggaagcacac ctacaacctg     360
accatcgcct ggtatcggat gggcgacaac tgcgccatcc ctattaccgt gatggagtac    420
accgagtgcc cctacaacaa gagcctggga gtgtgcccca tccggaccca gccccggtgg    480
agctactacg acagcttcag cgctgtgagc gaggacaacc tgggcttcct gatgcacgcc    540
cctgccttcg agaccgccgg cacctacctg cggctggtga agatcaacga ctggaccgag    600
atcacccagt tcatcctgga gcaccgcgcc agagccagct gcaaatacgc cctgcccctg    660
cggatccccc ctgccgcctg cctgaccagc aaggcctatc agcagggcgt gaccgtggac    720
agcatcggca tgctgccccg gttcatcccc gagaaccagc ggaccgtggc cctgtactct    780
ctgaagatcg ccggctggca cggccccaag ccccctaca ccagcaccct gctgcccccc     840
gagctgagcg acaccaccaa cgccacccag cccgagctgg tgcccgagga ccccgaggat    900
agcgccctgc tggaggatcc cgccggaaca gtgagcagcc agatcccccc caactggcac    960
atccctagca tccaggacgt ggccccccac cacgccccag ccgcccctag caaccccggc   1020
ctgatcatcg cgccctggcc ggcagcacc ctggccgccc tggtgatcgg cggcatcgcc    1080
ttttgggtgc gcagacgcgc ccagatggcc cccaagcggc tgcggctgcc ccacatccgc   1140
gacgacgacg cccctccatc tcaccagccc ctgttctag                          1179
```

<210> SEQ ID NO 2
<211> LENGTH: 314
<212> TYPE: PRT
<213> ORGANISM: Artificial Sequence
<220> FEATURE:
<223> OTHER INFORMATION: Truncated gD amino acid sequence

<400> SEQUENCE: 2

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
```

```
                        165                 170                 175
Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln
305                 310

<210> SEQ ID NO 3
<211> LENGTH: 392
<212> TYPE: PRT
<213> ORGANISM: Artificial Sequence
<220> FEATURE:
<223> OTHER INFORMATION: Full-length gD amino acid sequence

<400> SEQUENCE: 3

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
```

```
                210                 215                 220
Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
                260                 265                 270

Tyr Thr Ser Thr Leu Leu Pro Pro Glu Leu Ser Asp Thr Thr Asn Ala
            275                 280                 285

Thr Gln Pro Glu Leu Val Pro Glu Asp Pro Glu Asp Ser Ala Leu Leu
        290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
                340                 345                 350

Ala Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
370                 375                 380

Pro Pro Ser His Gln Pro Leu Phe
385                 390

<210> SEQ ID NO 4
<211> LENGTH: 393
<212> TYPE: PRT
<213> ORGANISM: Artificial Sequence
<220> FEATURE:
<223> OTHER INFORMATION: Full-length gD amino acid sequence variant #1

<400> SEQUENCE: 4

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
```

```
                180              185              190
Val Lys Ile Asn Asp Trp Thr Glu Ile Thr Gln Phe Ile Leu Glu His
            195              200              205
Arg Ala Arg Ala Ser Cys Lys Tyr Ala Leu Pro Leu Arg Ile Pro Pro
210              215              220
Ala Ala Cys Leu Thr Ser Lys Ala Tyr Gln Gln Gly Val Thr Val Asp
225              230              235              240
Ser Ile Gly Met Leu Pro Arg Phe Ile Pro Glu Asn Gln Arg Thr Val
            245              250              255
Ala Leu Tyr Ser Leu Lys Ile Ala Gly Trp His Gly Pro Lys Pro Pro
        260              265              270
Tyr Thr Ser Thr Leu Leu Pro Pro Glu Leu Ser Asp Thr Thr Asn Ala
        275              280              285
Thr Gln Pro Glu Leu Val Pro Glu Asp Pro Glu Asp Ser Ala Leu Leu
        290              295              300
Glu Asp Pro Ala Gly Thr Val Ser Ser Gln Ile Pro Pro Asn Trp His
305              310              315              320
Ile Pro Ser Ile Gln Asp Val Ala Pro His His Ala Pro Ala Ala Pro
            325              330              335
Ser Asn Pro Gly Leu Ile Ile Gly Ala Leu Ala Gly Ser Thr Leu Ala
            340              345              350
Val Leu Val Ile Gly Gly Ile Ala Phe Trp Val Arg Arg Arg Ala Gln
        355              360              365
Met Ala Pro Lys Arg Leu Arg Leu Pro His Ile Arg Asp Asp Asp Ala
370              375              380
Pro Pro Ser His Gln Pro Leu Phe Tyr
385              390
```

<210> SEQ ID NO 5
<211> LENGTH: 393
<212> TYPE: PRT
<213> ORGANISM: Artificial Sequence
<220> FEATURE:
<223> OTHER INFORMATION: Full-length gD amino acid sequence variant #2

<400> SEQUENCE: 5

```
Met Gly Arg Leu Thr Ser Gly Val Gly Thr Ala Ala Leu Leu Val Val
1                5               10               15
Ala Val Gly Leu Arg Val Val Cys Ala Lys Tyr Ala Leu Ala Asp Pro
            20              25               30
Ser Leu Lys Met Ala Asp Pro Asn Arg Phe Arg Gly Lys Asn Leu Pro
        35              40               45
Val Leu Asp Arg Leu Thr Asp Pro Pro Gly Val Lys Arg Val Tyr His
    50              55              60
Ile Gln Pro Ser Leu Glu Asp Pro Phe Gln Pro Pro Ser Ile Pro Ile
65              70              75              80
Thr Val Tyr Tyr Ala Val Leu Glu Arg Ala Cys Arg Ser Val Leu Leu
            85              90              95
His Ala Pro Ser Glu Ala Pro Gln Ile Val Arg Gly Ala Ser Asp Glu
        100             105             110
Ala Arg Lys His Thr Tyr Asn Leu Thr Ile Ala Trp Tyr Arg Met Gly
            115             120             125
Asp Asn Cys Ala Ile Pro Ile Thr Val Met Glu Tyr Thr Glu Cys Pro
        130             135             140
Tyr Asn Lys Ser Leu Gly Val Cys Pro Ile Arg Thr Gln Pro Arg Trp
```

```
                145                 150                 155                 160
Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
                180                 185                 190

Val Lys Ile Asn Asp Trp Thr Glu Ile Thr Gln Phe Ile Leu Glu His
                195                 200                 205

Arg Ala Arg Ala Ser Cys Lys Tyr Ala Leu Pro Leu Arg Ile Pro Pro
                210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
                260                 265                 270

Tyr Thr Ser Thr Leu Leu Pro Pro Glu Leu Ser Asp Thr Thr Asn Ala
                275                 280                 285

Thr Gln Pro Glu Leu Val Pro Glu Asp Pro Glu Asp Ser Ala Leu Leu
                290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
                340                 345                 350

Val Leu Val Ile Gly Gly Ile Ala Phe Trp Val Arg Arg Arg Ala Gln
                355                 360                 365

Met Ala Pro Lys Arg Leu Arg Leu Pro His Ile Arg Asp Asp Asp Ala
                370                 375                 380

Pro Pro Ser His Gln Pro Leu Phe Tyr
385                 390

<210> SEQ ID NO 6
<211> LENGTH: 393
<212> TYPE: PRT
<213> ORGANISM: Artificial Sequence
<220> FEATURE:
<223> OTHER INFORMATION: Full-length gD amino acid sequence variant #3

<400> SEQUENCE: 6

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
                20                  25                  30

Ser Leu Lys Met Ala Asp Pro Asn Arg Phe Arg Gly Lys Asn Leu Pro
                35                  40                  45

Val Leu Asp Gln Leu Thr Asp Pro Pro Gly Val Lys Arg Val Tyr His
                50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
                100                 105                 110

Ala Arg Lys His Thr Tyr Asn Leu Thr Ile Ala Trp Tyr Arg Met Gly
```

```
                    115                 120                 125
Asp Asn Cys Ala Ile Pro Ile Thr Val Met Glu Tyr Thr Glu Cys Pro
        130                 135                 140
Tyr Asn Lys Ser Leu Gly Val Cys Pro Ile Arg Thr Gln Pro Arg Trp
145                 150                 155                 160
Ser Tyr Tyr Asp Ser Phe Ser Ala Val Ser Glu Asp Asn Leu Gly Phe
                165                 170                 175
Leu Ile His Ala Pro Ala Phe Glu Thr Ala Gly Thr Tyr Leu Arg Leu
            180                 185                 190
Val Lys Ile Asn Asp Trp Thr Glu Ile Thr Gln Phe Ile Leu Glu His
                195                 200                 205
Arg Ala Arg Ala Ser Cys Lys Tyr Ala Leu Pro Leu Arg Ile Pro Pro
    210                 215                 220
Ala Ala Cys Leu Thr Ser Lys Ala Tyr Gln Gln Gly Val Thr Val Asp
225                 230                 235                 240
Ser Ile Gly Met Leu Pro Arg Phe Ile Pro Glu Asn Gln Arg Thr Val
                245                 250                 255
Ala Leu Tyr Ser Leu Lys Ile Ala Gly Trp His Gly Pro Lys Pro Pro
            260                 265                 270
Tyr Thr Ser Thr Leu Leu Pro Pro Glu Leu Ser Asp Thr Thr Asn Ala
        275                 280                 285
Thr Gln Pro Glu Leu Val Pro Glu Asp Pro Glu Asp Ser Ala Leu Leu
    290                 295                 300
Glu Asp Pro Ala Gly Thr Val Ser Ser Gln Ile Pro Pro Asn Trp His
305                 310                 315                 320
Ile Pro Ser Ile Gln Asp Val Ala Pro His His Ala Pro Ala Ala Pro
                325                 330                 335
Ser Asn Pro Gly Leu Ile Ile Gly Ala Leu Ala Gly Ser Thr Leu Ala
            340                 345                 350
Val Leu Val Ile Gly Gly Ile Ala Phe Trp Val Arg Arg Arg Ala Gln
        355                 360                 365
Met Ala Pro Lys Arg Leu Arg Leu Pro His Ile Arg Asp Asp Asp Ala
    370                 375                 380
Pro Pro Ser His Gln Pro Leu Phe Tyr
385                 390

<210> SEQ ID NO 7
<211> LENGTH: 393
<212> TYPE: PRT
<213> ORGANISM: Artificial Sequence
<220> FEATURE:
<223> OTHER INFORMATION: Full-length gD amino acid sequence variant #4

<400> SEQUENCE: 7

Met Gly Arg Leu Thr Ser Gly Val Gly Thr Ala Ala Leu Leu Val Val
1               5                   10                  15
Ala Val Gly Leu Arg Val Val Cys Ala Lys Tyr Ala Leu Ala Asp Pro
                20                  25                  30
Ser Leu Lys Met Ala Asp Pro Asn Arg Phe Arg Gly Lys Asn Leu Pro
            35                  40                  45
Val Leu Asp Gln Leu Thr Asp Pro Pro Gly Val Lys Arg Val Tyr His
        50                  55                  60
Ile Gln Pro Ser Leu Glu Asp Pro Phe Gln Pro Pro Ser Ile Pro Ile
65                  70                  75                  80
Thr Val Tyr Tyr Ala Val Leu Glu Arg Ala Cys Arg Ser Val Leu Leu
```

-continued

```
                85                  90                  95
His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
            115                 120                 125

Asp Asn Cys Ala Ile Pro Ile Thr Val Met Glu Tyr Thr Glu Cys Pro
            130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
            245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
            275                 280                 285

Thr Gln Pro Glu Leu Val Pro Glu Asp Pro Glu Asp Ser Ala Leu Leu
            290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
            325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
            370                 375                 380

Pro Pro Ser His Gln Pro Leu Phe Tyr
385                 390
```

THERAPEUTIC VACCINES FOR TREATING HERPES SIMPLEX VIRUS TYPE-2 INFECTIONS

CROSS-REFERENCE TO RELATED APPLICATIONS

This application claims priority to U.S. Provisional Application No. 61/749,682, filed Jan. 7, 2013, and U.S. Provisional Application No. 61/799,552, filed Mar. 15, 2013, both of which are hereby incorporated by reference in their entireties.

STATEMENT OF GOVERNMENT SUPPORT

This invention was made with government support under Grant Numbers R43/AI063820 and R44/AI063820 awarded by NIAID. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BMRI_006_02US_SeqList_ST25.txt, date recorded: Jan. 2, 2014, file size 22 kilobytes).

FIELD OF THE INVENTION

The invention is related to the fields of immunology, virology, and vaccine development. In particular, the invention relates to a heterologous immunization protocol comprising an intramuscular priming dose comprised of a DNA vaccine encoding an antigen, an intranasal boosting dose comprised of the protein form of the antigen encapsulated in liposomes, and a second boosting dose comprised of both the DNA vaccine and the liposomal-encapsulated protein antigen. This protocol is particularly effective in inducing a therapeutic immune response to herpes-simplex virus that reduces clinical symptoms associated with viral reactivation in infected subjects.

BACKGROUND OF THE INVENTION

Herpes simplex virus type 2 (HSV-2) is endemic in the human population and prevalent throughout the world. The World Health Organization estimated in 2003 that more than 300 million women and more than 200 million men were infected with HSV-2 (Cohen (2010) Science, Vol. 330: 304). According to the Centers for Disease Control and Prevention (CDC) approximately 20% of the US adult population is infected with HSV-2 (1), which can result in significant morbidity and psychological suffering. After initial replication in epithelial cells, virus enters neurons innervating the site of infection and enters latency. Periodically, HSV-2 will reactivate, replicate, form new viral particles and travel down the axon to the original infected site where it will undergo another round of lytic replication in the mucosal epithelium.

Recurrences of genital ulcers typically occur 4 times per year (2). Asymptomatic shedding of virus in the absence of vesicle formation is also a common occurrence. As many as 70% of new cases of HSV-2 are reported to be acquired from partners with asymptomatic shedding (3) and it is estimated that HSV-2 infected women shed virus from the genital tract a total of 15-20% of days (4). Although HSV-2 generally results in mucosal lesions, HSV-2 infections involving other organs and surfaces are not uncommon (5). For example, HSV-2 infection can involve the central nervous system where it induces the abrupt onset of fever and focal neurological symptoms. In addition, vertical transmission of virus from mother to infant and infections in immune compromised individuals can lead to viral encephalitis and/or dissemination of virus throughout the body (6). In the absence of treatment with nucleoside analogs, the mortality rate for these infants is 50% (6). In addition to causing primary disease on its own. HSV-2 is also a positive cofactor for HIV-1 transmission and has been associated with a 2-4 fold risk of acquiring HIV-1 (7).

While it should be feasible to develop protective immunity to HSV-2, a successful HSV-2 vaccine remains elusive. This is primarily due to the various ways in which HSV-2 interacts with the host immune system throughout its complicated replication cycle. Many different HSV-2 immunization strategies have been developed including the use of whole inactivated virus, live attenuated virus, live replication defective virus, subunit vaccines and DNA vaccines (Bernstein and Stanberry (1999) Vaccine, Vol. 17(13-14): 1681-1689; Krause and Straus (1999) Infect Dis Clin North Am., Vol. 13(1):61-81; McKenzie and Straus (1996) Rev Med. Virol., Vol. 6:85-96). To date, the only vaccine candidate that demonstrated any efficacy in humans provided only limited protection from HSV-2, and solely in female patients that are seronegative for herpes simplex virus type 1 (HSV-1) (8). Recently published results from a follow-up trial reported that this subunit vaccine was largely ineffective, contradicting the results of the earlier trial (Cohen (2010) Science, Vol. 330: 304). Thus, a safe and effective vaccine for HSV-2 is still lacking.

Clinical trials and animal studies have indicated that any successful HSV-2 vaccine candidate must initiate protection in multiple forms. Humoral immunity is important for protection from extracellular virion particles during initial exposure, during vertical transmission of virus from mother to child and during reactivation of virus when extracellular particles are transmitted from neuron to epithelial cell (9, 10). Infections in B cell-deficient mice indicate that while HSV-specific antibody limits infection, other arms of the immune system are required to prevent infection (11). Cellular immunity is necessary for clearance of virus-infected epithelial cells during primary and recurrent infections, resolution of lytic infections in sensory ganglia and possibly in the prevention of reactivation (12-18). Depletion studies have demonstrated that protection against HSV-2 re-infection is primarily controlled by $CD4^+$ T cells rather than $CD8^+$ T cells or antibody (19-21). Further, long term immunity appears to be dependent upon mucosal rather than systemic immunization, highlighting the importance of local mucosal immune responses (22).

It is well known that a HSV-2 vaccine candidate capable of protecting against diseases may not completely contain virus infection and replication. Therefore, it has been a real challenge for a successful HSV-2 vaccine to provide protection against both primary HSV-2 infection-caused acute diseases and the subsequent development of latency and recurrence. In animal studies, some previous HSV-2 vaccine candidates have substantially reduced viral replication in the genital tract and significantly prevented the symptoms of disease resulting from primary infection. However, the immunity elicited by these vaccines can only partially protect against latent infection and recurrent disease (3-10).

Vaccine induced host immune responses may act at one or more key steps to prevent or limit genital HSV infection. To prevent both acute disease and the establishment of latency, ideally immune responses elicited by a HSV-2 vaccine would be able to effectively contain the HSV-2 virus replication at the genital mucosae and successfully prevent virus transmission to sensory nerve endings. In order to obtain maximum protection against initial viral replication, it is most likely that a vaccine would need to induce broad and potent protective immunity, especially robust mucosal immune responses at genital sites. A therapeutic vaccine to treat those already infected with HSV-2 would ideally elicit immune responses capable of containing viral shedding and controlling clinical recurrences. At a minimum, a therapeutic vaccine should reduce the frequency, duration and severity of clinical recurrences and viral shedding.

Thus, there remains a clear need in the art for the development of a safe and effective therapeutic and prophylactic vaccine for HSV-2 due to the magnitude of the public health problem and the failure of antiviral drugs to prevent its spread.

SUMMARY OF THE INVENTION

The present invention is based, in part, on the discovery of a new heterologous immunization regimen that induces a therapeutic immunity against HSV-2 and effectively treats subjects with an established HSV-2 infection. This therapeutic vaccine comprises a priming dose of a nucleic acid encoding an HSV-2 antigen, an initial or first boosting dose comprising the protein form of the antigen encapsulated in liposomes, and one or more subsequent boosting doses comprising both the nucleic acid encoding the HSV-2 antigen and the liposomal-encapsulated protein antigen. This immunization protocol induces high titers of mucosal antigen-specific IgG and IgA antibodies and an effective T cell response, which reduces viral shedding from the genital tract and significantly reduces the recurrence of herpetic lesions in infected subjects. Accordingly, the present invention provides a method for treating an HSV-2 infection in an animal (e.g., mammal), particularly a human.

In one embodiment, the method comprises administering to the animal a priming preparation comprising a nucleic acid encoding an HSV-2 antigen, a first boosting preparation comprising the HSV-2 antigen encapsulated in liposomes, and a second boosting preparation comprising the nucleic acid encoding the HSV-2 antigen and the liposomal-encapsulated HSV-2 antigen. In certain embodiments, the nucleic acid encoding the HSV-2 antigen is administered intramuscularly and the liposomal-encapsulated antigen is administered intranasally. The first boosting preparation may be administered about 2 to 4 weeks, for example, 7 to 18 days, following administration of the priming preparation. In similar embodiments, the second boosting preparation may be administered about 2 to 4 weeks, such as 7 to 18 days, following administration of the first boosting preparation.

One or more symptoms of HSV-2 infection can be ameliorated in the animal following administration of the second boosting preparation. For instance, in one embodiment, the recurrence of herpetic lesions is reduced and/or prevented in the animal as compared to an untreated animal or an animal immunized with a non-mucosal vaccine. In another embodiment, viral shedding from the genital tract is reduced in the animal as compared to an untreated animal or an animal immunized with a non-mucosal vaccine. In certain embodiments, the method further comprises administering to the animal a combination of the nucleic acid encoding the HSV-2 antigen and the HSV-2 antigen encapsulated in liposomes at the sign of recurrence of herpetic lesions. In such embodiments, the nucleic acid is preferably administered intramuscularly and the liposomal-encapsulated antigen is administered intranasally.

The present invention also includes a method of eliciting a protective immune response against HSV-2 in an animal (e.g. mammal), particularly a human, prior to infection with the virus. In one embodiment, the method comprises administering to the animal a priming preparation comprising a nucleic acid encoding an HSV-2 antigen, a first boosting preparation comprising the HSV-2 antigen encapsulated in liposomes, and a second boosting preparation comprising the nucleic acid encoding the HSV-2 antigen and the liposomal-encapsulated HSV-2 antigen. In some embodiments, the nucleic acid encoding the HSV-2 antigen is administered intramuscularly and the liposomal-encapsulated antigen is administered intranasally. The protective immune response may be biased towards a Th1 type immune response and may comprise neutralizing antibodies in the serum and vaginal secretions, mucosal IgA and/or mucosal IgG responses, and an increase in viral clearance.

In certain aspects of the invention, the nucleic acid in the priming and second boosting preparation is a vector encoding an HSV-2 antigen under the control of a promoter, such as a cytomegalovirus promoter. In one embodiment, the HSV-2 antigen encoded by the vector is a gD glycoprotein. The gD glycoprotein may be the full-length protein or a truncated protein comprising an immunogenic fragment or domain. In some embodiments, the sequence encoding the HSV-2 antigen (e.g. gD glycoprotein) is codon-optimized for expression in mammalian cells, particularly human cells.

In another aspect of the invention, the HSV-2 antigen in the first and second boosting preparations is encapsulated in anionic liposomes. The liposomes may have an average diameter of about 0.5-5 µm. In certain embodiments, the HSV-2 antigen encapsulated in liposomes in the boosting preparations is a gD glycoprotein, which may be the full-length protein or an immunogenic fragment thereof. In one particular embodiment, the HSV-2 antigen is an extracellular domain of a gD glycoprotein (e.g. amino acids 1-314 of the gD glycoprotein). In one embodiment, the liposomes used in the boost preparations consist of lipids, i.e. the liposomes do not contain additional proteins, ligands, or adjuvants. In another embodiment, the liposomes are non-fusogenic liposomes (i.e. do not contain any viral proteins incorporated into the liposomal membrane).

The present invention also includes kits for eliciting a therapeutic or protective immune response against HSV-2 in an animal (e.g. human). In one embodiment, the kit comprises a first immunizing component comprising a nucleic acid sequence encoding an HSV-2 antigen (e.g. gD glycoprotein), a second immunizing component comprising the HSV-2 antigen encapsulated in liposomes, and an instruction for a user to administer to the animal the first immunizing component, followed by administration of the second immunizing component, followed by administration of a combination of the first and second immunizing components to elicit the therapeutic immune response in the animal. In some embodiments, the first immunizing component is formulated for intramuscular administration, and the second immunizing component is formulated for intranasal administration. In some embodiments, the animal is human. In one particular embodiment, the human is infected with HSV-2. In another embodiment, the human is at risk of infection with HSV-2.

DETAILED DESCRIPTION OF THE INVENTION

Figure 1:
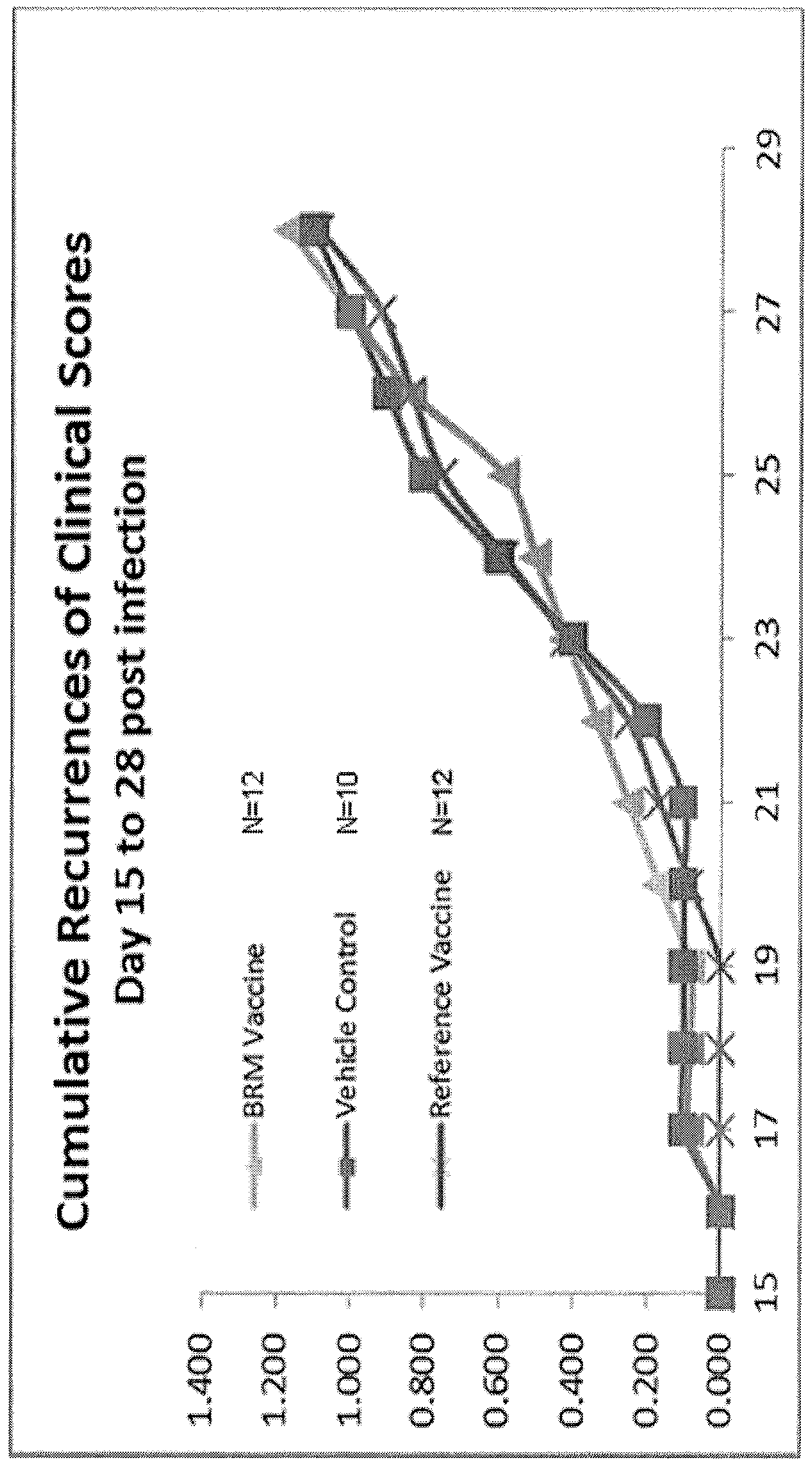
FIG. 1. Cumulative recurrences of clinical scores in guinea pigs 15 to 28 days post-infection with HSV-2 prior to treatment. HSV-2-infected animals were randomly divided into three treatment groups (BRM vaccine, vehicle control, and reference vaccine). There was no significant difference among the three groups in the rate of recurrences prior to treatment (p=0.95; day 15-28 slopes: BRM vaccine=0.08646±0.008142; vehicle control=0.08989±0.009964; reference vaccine=0.08992±0.008480). Y-axis: cumulative numbers of recurrent herpatic lesions per animal (in each group); X-axis: days post-infection.

Many different HSV-2 immunization strategies have been developed and evaluated, including the use of whole inactivated virus, live attenuated virus, live replication defective virus, subunit vaccines and DNA vaccines. However, a safe and effective vaccine for HSV-2 is still not available. The present invention is based, in part, on the discovery of a new HSV-2 vaccine that elicits protective and therapeutic immunity against HSV-2. As described in detail herein, the inventors have developed a heterologous immunization protocol comprised of an intramuscular priming dose of a DNA vector encoding an HSV-2 antigen, followed by an initial boost of a liposomal-encapsulated protein form of the antigen delivered mucosally (e.g. intranasally), followed by one or more subsequent boosts with both the DNA vector and the liposomal-encapsulated antigen. This protocol is particularly effective in inducing a therapeutic immune response to treat subjects who are already infected with HSV-2. The therapeutic vaccine induces a synergistic immune response comprised of humoral, T cell, and mucosal immunity. Specifically, the vaccine stimulates high titers of vaginal antigen-specific IgG and IgA antibodies, a Th1-biased immune response, and high titers of serum antigen-specific IgG. In addition, the therapeutic vaccine is superior to a subcutaneously-administered vaccine comprising an HSV-2 gD antigen in its ability to prevent or reduce recurrences of herpatic lesions and reduce viral shedding.

Thus, the present invention provides a method for eliciting a therapeutic immune response against HSV-2 in an animal, such as a mammal. The goal of therapeutic vaccination is to target immune responses in an infected individual to eradicate cells already infected with virus or prevent the latent viruses from reactivation and trafficking back to the original infection sites. As used herein, "therapeutic immunity" or a "therapeutic immune response" refers to immunity or eliciting an immune response against an infectious agent that ameliorates or eliminates an infection or reduces at least one symptom thereof. Specifically, induction of a therapeutic immune response from administration of the vaccine is evident by elimination or reduction of the presence of one or more symptoms of disease induced by the infectious agent or a reduction in the duration or severity of such symptoms. For instance, in one embodiment, therapeutic immunity against HSV-2 refers to immunity that reduces the severity or duration of a HSV-2 infection. Therapeutic immunity, in some embodiments, is manifested by elimination or reduction of the presence of one or more symptoms of HSV-2-induced disease. Clinical symptoms of HSV-2-induced disease include blister-like sores or ulcerations around the genital and/or rectal areas (e.g. herpatic lesions), a rash or small bumps on the skin in the genital and/or rectal areas, painful urination, vaginal fluid discharge, and flu-like symptoms (e.g., fever and swollen lymph glands in the groin). In some embodiments, an effective therapeutic immune response reduces the amount of viral shedding from the genital mucosa.

In one embodiment, the present invention provides a method for treating an HSV-2 infection in an animal (e.g. mammal, human) comprising administering to the animal a priming preparation comprising a nucleic acid (e.g. vector) encoding an HSV-2 antigen, a first boosting preparation comprising the HSV-2 antigen encapsulated in liposomes, and a second boosting preparation comprising the nucleic acid encoding the HSV-2 antigen and the HSV-2 antigen encapsulated in liposomes. In certain embodiments, the nucleic acid (e.g. vector) is administered intramuscularly and the liposomal-encapsulated protein antigen is administered mucosally. Mucosal routes of administration include, but are not limited to, intranasal, oral, vaginal, rectal, sublingual, buccal, or via inhalation to the lungs. In one particular embodiment, the liposomal-encapsulated protein antigen is administered intranasally. In some embodiments, the HSV-2 antigen used in the treatment method is a gD glycoprotein.

Preferably, one or more symptoms of HSV-2 infection is alleviated, ameliorated, reduced, or cured following administration of the heterologous prime and boost HSV-2 vaccine, particularly following administration of the second boosting preparation. For instance, the number, severity or frequency of genital lesions (i.e. herpatic lesions) is significantly reduced in an immunized animal as compared to an untreated animal or an animal vaccinated with a non-mucosal vaccine. In one embodiment, the recurrence of herpatic lesions is reduced or completely prevented in the immunized animal as compared to an untreated animal or animal vaccinated with a non-mucosal vaccine. In another embodiment, viral shedding from the genital tract is reduced in the immunized animal as compared to an untreated animal or animal vaccinated with a non-mucosal vaccine. As used herein, "non-mucosal vaccine" refers to any vaccine against HSV-2 that is administered to the subject by a route other than a mucosal route. In some embodiments, a non-mucosal vaccine comprises an HSV-2 protein antigen or a nucleic acid encoding the HSV-2 antigen that is administered intramuscularly, intravenously, intraperitoneally, intradermally, or subcutaneously. In one embodiment, a non-mucosal vaccine comprises a truncated HSV-2 gD protein (e.g., gD extracellular domain) formulated for subcutaneous administration.

Other viruses that establish long-term infections, which can be treated with the methods and kits of the present invention, include human papilloma virus (HPV), the hepatitis B and C viruses (HBV, HCV), and human immunodeficiency virus (HIV). The development of therapeutic vaccines for viruses has focused on the activation of CTL to recognize and destroy infected cells and/or controlling the virus spread. The methods of the invention are effective in enhancing cellular immune responses, making them suitable for providing therapeutic vaccination. The effectiveness of the methods may be further enhanced by inclusion of cytokine adjuvants and CpG motifs that have been shown to be particularly promising in the development of anti-cancer vaccines (Belardelli et al., Cancer Res. 64:6827-6830 (2004)).

The present invention also provides a kit for eliciting a therapeutic immune response against HSV-2 in an animal (e.g. mammal). In one embodiment, the kit comprises a first immunizing component comprising a nucleic acid sequence encoding an HSV-2 antigen, a second immunizing component comprising the HSV-2 antigen encapsulated in liposomes, and an instruction for a user to administer to the animal the first immunizing component, followed by administration of the second immunizing component, followed by administration of a combination of the first and second immunizing components to elicit the therapeutic immune response in the animal. In some embodiments, the first immunizing component is formulated for intramuscular administration and the second immunizing component is formulated for mucosal administration, for instance intranasally, orally, intravaginally, rectally, sublingually, buccally or via inhalation. In certain embodiments, the second immunizing component is formulated for intranasal administration. In another embodiment, the kits further comprise a delivery device for administering the first immunizing component, the second immunizing component, or both. The delivery device can be any of the delivery devices described infra, including droppers, swabs, aerosolizers, insufflators, nebulizers, inhalers, syringes equipped with needles or auto-injectors.

The methods and the kits of the invention are also useful for prophylactic vaccination (i.e. inducing a protective immune response in an animal). The present invention provides a method for eliciting a protective immune response against HSV-2 in an animal, such as a mammal. In one embodiment, the method comprises administering to the mammal a priming preparation comprising a nucleic acid (e.g. vector) encoding an HSV-2 antigen, a first boosting preparation comprising the HSV-2 antigen encapsulated in liposomes, and a second boosting preparation comprising the nucleic acid encoding the HSV-2 antigen and the HSV-2 antigen encapsulated in liposomes. In certain embodiments, the nucleic acid (e.g. vector) encoding the HSV-2 antigen is administered intramuscularly and the liposomal-encapsulated HSV-2 protein antigen is administered mucosally, such as intranasally, orally, intravaginally, rectally, sublingually, buccally or via inhalation. In one particular embodiment, the liposomal-encapsulated HSV-2 protein antigen is administered intranasally. In such embodiments, the method induces high titers of serum and vaginal antibodies with high neutralizing activities, a Th1 type biased response, and potent protective immunity at the vaginal cavity, the portal of entry for the HSV-2 virus.

As used herein, a "protective immune response" or "protective immunity" refers to immunity or eliciting an immune response against an infectious agent, which is exhibited by a vertebrate (e.g., a human), that prevents or protects against infection. A protective immune response that prevents or protects against the appearance of disease symptoms will reduce or stop the spread of HSV-2 in a population by reducing viral shedding. In some embodiments, the protective immunity induced by the vaccine of the present invention is a sterilizing immunity. "Sterilizing immunity" is an immune response that completely eliminates or prevents an infection or is rapidly cleared, leaving no detectable trace.

The present invention further provides a method for modulating immune responses such that a desired immune response biased towards a T helper type 1 (Th1) response may be elicited in an animal. The method comprises administering to the animal a priming preparation comprising a nucleic acid sequence encoding an antigen, such as an HSV-2 antigen, administering to the animal a first boosting preparation comprising the antigen encapsulated in liposomes, and subsequently administering a second boosting preparation comprising a combination of the nucleic acid encoding the antigen and the liposomal-encapsulated protein antigen. In certain embodiments, the nucleic acid encoding the antigen is administered intramuscularly and the liposomal-encapsulated protein antigen is administered mucosally (e.g. intranasally). "Biased towards" refers to the situation where the observed immune response is closer to a Th1 or T helper type 2 (Th2) response as compared to the response before immunization. In certain embodiments, immunization will completely switch a Th2 response to a Th1 response. In other embodiments, immunization may not completely switch a Th2 response to a Th1 response, but instead, results in a mixed or balanced response or a weaker Th2 response.

Most immune responses are regulated by T lymphocytes, which initiate and shape the nature of the response. As immune responses mature, $CD4^+$ T lymphocytes can become polarized towards T helper type 1 (Th1) or T helper type 2 (Th2) immune responses. The hallmark of Th1 and Th2-type responses is the predominant pattern of cytokines that are present. Th1 responses are characterized by high levels of IFN-γ and low levels of IL-4 and IL-10, while Th2 responses are characterized by low levels of IFN-γ and high levels of IL-4 and IL-10. These cytokines play an important role in determining the functional capabilities of the T cells. Th2-type responses lead to the preferred production of antibodies of the IgG1 subclass, with little or no generation of CTLs. Th1-type responses lead to the preferred production of antibodies of the IgG2a subclass and induction of CTLs that can effectively kill cells infected with viruses or other organisms.

Table 1 below summarizes the immunological characteristics of Th1 and Th2 polarized immune responses. Th1 polarized responses are typically generated during infections with viruses or bacteria. In contrast, Th2 polarized responses are often observed in parasitic infections, in allergic responses, and by conventional alum-based intramuscularly delivered protein vaccines that are used in humans. Genetics can also determine the type of immune responses generated. For example, Th1 responses predominate in the C57BL/6 strain of mouse, while Th2 responses predominate in the Balb/c strain of mouse. Immune responses may also consist of both Th1 and Th2 components, affording protection by both humoral and cell mediated arms of the immune response. Direct determination of the frequencies of cytokine producing cells is accomplished by the use of ELISPOT (Enzyme Linked Immunosorbent SPOT assays) or by immunofluorescence staining to reveal intracellular cytokine production. Serum IgG1:IgG2a ratios are also widely accepted and followed criteria to determine T helper types (Table 1). An IgG1 to IgG2a ratio for balanced Th1 and Th2 response would be between 0.5 and 2.0.

TABLE 1

A Characteristics of Th1 and Th2 polarized T cell responses.

| Immune Responses | Th1-type immune responses | Th2-type immune responses |
| --- | --- | --- |
| Humoral immunity | Serum IgG1/IgG2a < 0.5 | Serum IgG1/IgG2a > 2.0 |
| T cell cytokine secretion | ↑ IFN-γ; ↓ IL-10 and IL-4 | ↑ IL-10 and IL-4; ↓ IFN-γ |
| CTL | High | Low or absent |
| Prototypical mouse strains | C57BL/6 | Balb/c |

As used herein, "T helper type 1 response" and "Th1 response" are used interchangeably to refer to a range of host animal responses including one or more, usually all the characteristics listed in the middle column of Table 1 above. These characteristics include a ratio of IgG1:IgG2a of no greater than 0.5; increased IFN-γ (and other Th1 cytokines) secretion by T helper 1 cells and decreased IL-10 and IL4 (and other Th2 cytokines) secretion by T helper 2 cells; and high CTL activity.

Similarly, as used herein, "T helper type 2 response" and "Th2 response" are used interchangeably to refer to a range of host animal responses including one or more, usually all the characteristics listed in the right column of Table 1 above. These characteristics include a ratio of IgG1:IgG2a of no less than 2.0; decreased IFN-γ (and other Th1 cytokines) secretion by T helper 1 cells and increased IL-10 and IL-4 (and other Th2 cytokines) secretion by T helper 2 cells; and low or absent CTL activity.

The instant invention additionally provides a method to develop effective vaccines and vaccination protocols to specifically target the most common entry portal for microorganisms, the mucosal surfaces of the body. The invention provides that vaccines could be made more effective by encapsulating them into liposomes with a defined composition/size, and by delivering them directly to mucosal surfaces. By combining liposome encapsulated vaccines with appropriate immunization regimens, immune responses can be tailored to provide more effective and specific vaccines. In certain embodiments, the ideal vaccine generates a balanced or T helper 1 (Th1)-biased immune response that also includes robust antibody responses, CTL generation and Th1-type cytokine production, and local immunity at mucosal sites. In other embodiments, it may be possible to tailor the immune response to generate a T helper 2 (Th2)-biased immune response, which may be beneficial in preventing rejection in graft hosts and in protecting against certain parasitic infections.

In one aspect, the present invention provides methods, reagents, and kits for effectively eliciting immune responses, such as protective and therapeutic immune responses in animals, especially mammals (e.g. humans), against certain antigens, such as viral antigens (e.g. HSV-2 antigens). One salient feature of the invention relates to the use of liposome-encapsulated protein antigens delivered mucosally (e.g. intranasally (IN)) or intramuscularly (IM) to the host animal.

One component of the methods and kits of the present invention is the use of a "priming" immunization, comprising the initial administration of one or more antigens to an animal, especially a human patient, in preparation for subsequent administrations of the same antigen. Specifically, the term "priming," as used herein, refers to a first immunization using an antigen which induces an immune response to the desired antigen and recalls a higher level of immune response to the desired antigen upon subsequent reimmunization with the same antigen when administered in the context of the same or a different vaccine delivery system.

Another component of the methods and kits of the present invention is the use of a "boosting immunization," or a "boost," which means the administration of a composition delivering the same antigen as encoded in the priming immunization. A boost is sometimes referred to as an anamnestic response, i.e. an immune response in a previously sensitized animal. Multiple boosts can be administered, utilizing the same or differing amounts for each boost. A boosting that uses an antigen-delivery system different from the priming can be referred to as a "heterologous boost," whereas a boosting that uses the same antigen-delivery system as the priming can be referred to as a "homologous boost."

As an alternative to sequential administration as described above, the priming preparation and the boosting preparation may be administered simultaneously, i.e. at substantially the same time. The methods of the invention lead to potent synergistic effects between the priming immunization and the boosting immunization(s) in terms of immune responses the methods are able to elicit in an animal. As a result, the methods of the invention enable one to elicit a desired level of immune response, where each of the priming preparation and the boosting preparation(s), when administered alone to the animal, is insufficient to accomplish the desired level of immune response. In some embodiments, the heterologous immunization methods of the invention generate a therapeutic immune response characterized by an increase in cytotoxic T lymphocytes (CTL) and increase in antigen-specific IgG and IgA in vaginal secretions as compared to an untreated/non-immunized animal or an animal vaccinated with a non-mucosal vaccine. In other embodiments, the heterologous immunization methods as described herein reduces or completely prevents the recurrence of herpatic lesions and/or reduces viral shedding from the genital tract as compared to that observed in untreated/non-immunized animals or an animals vaccinated with a non-mucosal vaccine.

The effects of immune response in the host animal, including humoral and cellular immune responses, can be assessed by various assays known in the art. The humoral immune response includes total antigen-specific antibody (immunoglobulins, i.e., Ig) titers in serum or at mucosal surfaces; titers of HSV-2 antigen-specific antibodies in serum or at mucosal surfaces; titers of specific antibody isotypes and/or sub-types including IgG, IgA, IgG1, and IgG2a; ratio of IgG1 and IgG2a. Antigen-specific antibody titers can be measured by routine methods known in the art, such as ELISA assays. The cellular immune response includes cytotoxic T cell (CTL) phenotype and activity. Cellular immune response also includes secretion of cytokines characteristic of Th1 responses including IFN-γ, and secretion of cytokines characteristic of Th2 response including IL-10 and IL-4. The cytokines are detected directly by cytokine ELISPOT and/or ELISA assays (i.e., IFN-γ, IL-10 and/or IL-4) and inferred from IgG1:IgG2a ratios (e.g., Th1 versus Th2 response). Neutralization activity of serum and mucosal antibodies can be measured by various methods including complement-dependent neutralization assays as described in the Examples. The degree of HSV-2 viral latency in the nervous system can be assessed by, for example, quantitative real-time PCR (qPCR) analysis of dorsal root ganglia cells. The number of viral copies detected correlates to HSV-2 viral integration in the host, neuronal cell.

The nucleic acid encoding the antigen (e.g. HSV-2 antigen) and the protein antigen (e.g. liposomal-encapsulated antigen) may be administered by any one of the following routes: subcutaneously, intramuscularly, intradermally and mucosally, including using electronic/mechanical devices and/or methods such as electroporation. Exemplary routes of mucosal administration include, but are not limited to, intranasal, oral, vaginal, rectal, sublingual, buccal, or via inhalation. The nucleic acid encoding the antigen and the protein antigen may be administered by the same route, or by different routes. In certain preferred embodiments, the nucleic acid (e.g. vector) encoding the antigen is administered intramuscularly and the protein antigen (e.g. liposomal-encapsulated protein antigen) is administered intranasally, which results in not only an induction of a CTL response, but also in a robust mucosal immune response. In certain embodiments, the nucleic acid encoding the antigen is present in the priming preparation. The nucleic acid encoding the antigen may also be present in one or more boosting preparations following the initial or first boosting preparation, which typically comprises only the protein antigen (e.g. liposomal-encapsulated protein antigen). In particular embodiments, boosting preparations subsequent to the initial or first boosting preparation comprise two components: (1) a nucleic acid encoding the antigen, such as a vector, and (2) a protein form of the antigen, such as the protein antigen encapsulated in liposomes. Preferably, the two components are in separate formulations such that the two components can be administered by separate routes. For instance, in some embodiments, the nucleic acid component of the second boosting preparation is administered intramuscularly, whereas the protein component of the second boosting preparation is administered intranasally.

The present invention also contemplates devices for dispensing the priming and boosting preparations described herein for use in the methods and kits of the invention. For example, for embodiments in which the boosting preparation or the protein component of the boosting preparation is delivered intranasally, dispensing devices for intranasal formulations may, for example, take the form of an aerosol delivery system, and may be arranged to dispense only a single dose, or a multiplicity of doses. Such a device would deliver a metered dose of the boosting preparation to the nasal passage. Other examples of appropriate devices include, but are not limited to, droppers, swabs, aerosolizers (e.g. VaxINator™), insufflators (e.g. Valois Monopowder Nasal Administration Device, single dose Bespak UniDose DP dry powder intranasal delivery device), nebulizers, and inhalers. The devices may deliver the boosting preparation or the protein component of the boosting preparation by passive means requiring the subject to inhale the formulation into the nasal cavity. Alternatively, the device may actively deliver the boosting preparation or the protein component of the boosting preparation by pumping or spraying a dose into the nasal cavity. The boosting preparation or the protein component of the boosting preparation may be delivered into one or both nostrils by one or more such devices. Administration could include two devices per subject (one device per nostril). In embodiments in which the priming preparation or the nucleic acid component of a boosting preparation is delivered intramuscularly, devices, such as autoinjectors or pen-injectors, may be used to deliver the injection.

Different intervals between the priming preparation and the first boosting preparation may be used. The first boosting preparation can be administered 2-8 weeks, preferably 4-6 weeks, or more preferably about 2-4 weeks following the administration of the primary preparation. In one embodiment, the first boosting preparation is administered about 7 to about 18 days after the priming preparation. In another embodiment, the first boosting preparation is administered about 10 to about 16 days after the priming preparation.

Different intervals between boosting preparations (e.g. the first boosting preparation and the second boosting preparation) may also be used and they may be the same as or different from the interval between administration of the priming preparation and the first boosting preparation. For instance, the second boosting preparation (or subsequent boosting preparation) can be administered 2-8 weeks, preferably 4-6 weeks, or more preferably about 2-4 weeks following the administration of the first boosting preparation or previous boosting preparation. In one embodiment, the second boosting preparation is administered about 7 to about 18 days after the first boosting preparation (or previous boosting preparation). In another embodiment, the second boosting preparation is administered about 10 to about 16 days after the first boosting preparation (or previous boosting preparation). Multiple boosting preparations may be administered to the animal (e.g. mammal, human) following administration of the priming preparation and the first boosting preparation. In preferred embodiments, the subsequent boosting preparations comprise both a nucleic acid antigen component (i.e. nucleic acid encoding the antigen) and a protein antigen component (e.g. a liposomal-encapsulated protein antigen). In some embodiments, a subsequent boosting preparation comprising these two components is administered to the animal at the sign of one or more symptoms of viral infection. For instance, in embodiments in which the viral infection is HSV-2, a subsequent boosting preparation comprising a nucleic acid encoding an HSV-2 antigen and a liposomal-encapsulated HSV-2 protein antigen is administered to the animal at the sign of recurrence of genital lesions (i.e. herpatic lesions).

The invention contemplates that the total dose of antigen in the priming preparation or the boosting preparations, or both, may be administered to the animal in one or more administrations. For instance, the priming preparation may be administered over the course of two or three days. In one embodiment, the priming comprises one or two administrations separated by about 3 to 6 weeks, the first boosting preparation is administered about 3 to 10 weeks following the last priming administration, and the second boosting preparation is administered about 3 to 10 weeks following the first boosting. In another embodiment, the priming comprises one or two administrations separated by 3 days, the first boosting preparation is administered 3 weeks following the last priming administration, and the second boosting preparation is administered about 3 weeks following the first boosting. In a certain embodiment, the priming comprises two administrations separated by a day (e.g. prime preparation administered on day 1 and day 3), the first boosting preparation is administered 2-3 weeks following the last priming administration, and the second boosting preparation is administered 2-3 weeks following the first boosting.

The initial boost administration and the subsequent boosting administrations may use the same or different amounts of protein antigen (e.g. liposomal-encapsulated protein antigen), and the subsequent boost and the initial boost administrations can be administered via the same or different routes. The initial, priming administration and the boost administration(s) may use the same or different amounts of nucleic acid antigen (e.g., vector encoded antigen) delivered according to the same or different schedules. In some embodiments, the dose of nucleic acid antigen in the priming preparation is delivered over one or more administrations (e.g. two administrations, over the course of three days) and the dose of nucleic acid antigen in a boosting preparation is delivered in one administration (e.g. all in one day). The amount of nucleic acid antigen may be the same as or different than the amount of protein antigen delivered in the boosting preparations.

As used herein, the terms "antigen" or "immunogen", used interchangeably, are intended to encompass all peptide or protein sequences which are capable of inducing an immune response within the animal concerned. The terms "antigen" or "immunogen" encompass peptide or protein analogs of known or wild-type antigens, which analogs may be more soluble or more stable than wild type antigen, and which may also contain mutations or modifications rendering the antigen more immunologically active or optimized for expression in certain cell types (i.e. humanized codon usage). An antigen may also be a peptide in which particular amino acid substitutions have been made to a naturally-occurring antigen that alter protein structure, a portion of the naturally-occurring antigen including known protective epitopes (i.e. CTL epitopes), or a synthetically derived string of known epitopes that may or may not be limited to one pathogen (multivalent vaccine).

Further peptides or proteins that have sequences homologous with a desired antigen's amino acid sequence, where the homologous antigen induces an immune response to the respective pathogen, are also useful. Genes that are homologous to the desired antigen-encoding sequence should be construed to be included in the instant invention provided they encode a protein or polypeptide having a biological activity substantially similar to that of the desired antigen.

Analogs of the antigens described herein can differ from naturally occurring proteins or peptides by conservative amino acid, sequence differences or through modifications that do not affect sequence, or by both. For example, conservative amino acid changes may be made, which although they alter the primary sequence of the protein or peptide, do not normally alter its function. Modifications (which do not normally alter primary sequence) include in vivo, or in vitro chemical derivatization of polypeptides, e.g., acetylation, or carboxylation. Also included as antigens are proteins modified by glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also included as antigens according to this invention are sequences which have phosphorylated amino acid residues, e.g., phosphotyrosine, phosphoserine, or phosphothreonine. Also included as antigens are polypeptides that have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The antigens of the invention are not limited to products of any of the specific exemplary processes listed herein.

An antigen can be a full-length or a truncated antigen, an immunogenic fragment thereof, or an epitope derived from the antigen. In certain embodiments, the pathogen-specific antigen in the boosting preparations may be in the form of an attenuated or killed pathogen. Effective antigens also include surface antigens of these pathogens.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence or stimulates a cellular immune response. The term "epitope" encompasses sequences identical to the native sequence, as well as modifications to the native sequence, such as deletions, additions and substitutions (generally conservative in nature). The antigens used in the invention may comprise only a single epitope, such as, for example, a single CTL epitope.

The antigens encoded by the nucleic acids in the priming preparation or boosting preparations and the protein antigens in the boosting preparations preferably have overlapping epitopes. In certain embodiments, the two antigens may be identical to each other. Alternatively, the two antigens may have overlapping but different set of epitopes. By way of an illustrative example, in a vaccination protocol for HSV-2, a DNA encoding an HSV-2 glycoprotein may be used in the priming preparation, and the boosting preparation may be inactivated HSV-2. By way of another illustrating example, the priming preparation may be a vector encoding an HSV-2 antigen, and the boosting preparation may comprise a protein form of the antigen, or vice versa.

In certain embodiments, the antigen is an HSV-2 antigen. Suitable HSV-2 antigens include, but are not limited to, gH, gL, gM, gB, gC, gK, gE, or gD glycoproteins or derivatives thereof or Immediate Early proteins such as ICP27, ICP 47, ICP4, or ICP36. In one embodiment the HSV-2 antigen is a gD glycoprotein. The gD glycoprotein may be the full-length form of the protein (e.g. SEQ ID NO: 3) or a truncated form, such as the extracellular domain of gD, or immunogenic fragments thereof. The truncated forms of HSV-2 glycoproteins (e.g., gD glycoprotein) can include truncated forms that are secreted by cells expressing the glycoprotein. For instance, in some embodiments, the antigen is the extracellular domain of gD consisting of amino acids 1-314 of gD protein. In other embodiments, the antigen is the extracellular domain of gD comprising the amino acid sequence of SEQ ID NO: 2. Variants of the full-length or truncated forms of gD can also be used. For instance, in one embodiment, the gD glycoprotein comprises a sequence of SEQ ID NO: 4, SEQ ID NO: 5, SEQ ID NO: 6, or SEQ ID NO: 7. The full-length or truncated forms of HSV-2 glycoproteins (e.g. gD glycoprotein) may comprise signal peptides and/or purification tags (e.g. histidine or c-myc tags). In certain embodiments, the sequence encoding the antigen is optimized for expression in mammalian cells, such as human cells. For instance, for optimization in human cells, cis-acting motifs, such as internal TATA-boxes, chi-sites, ribosomal entry sites, AT-rich or GC-rich sequence stretches, ARE, INS, CRS sequence elements, cryptic splice donor and acceptor sites, and branch points, are eliminated or reduced in number from the antigen-encoding sequence. In one embodiment, a suitable human codon-optimized gD sequence comprises the sequence of SEQ ID NO: 1.

The following are illustrative examples of additional antigens that may be used in the methods of the present invention to induce protective or therapeutic immunity against other pathogens using the methods of the invention.

The antigens may be derived from HIV-1, (such as tat, nef, gp120 or gp 160, gp40, p24, gag, env, vif, vpr, vpu, rev), human herpes simplex virus type 1 (HSV-1) (such as gH, gL gM gB gC gK gE or gD or derivatives thereof or Immediate Early protein such as ICP27, ICP 47, ICP 4, ICP36), cytomegalovirus, especially Human, (such as gB or derivatives thereof), Epstein Barr virus (such as gp350 or derivatives thereof), Varicella Zoster Virus (such as gpI, II, III and IE63), or from a hepatitis virus such as hepatitis B virus (for example Hepatitis B Surface antigen or Hepatitis core antigen or pol), hepatitis C virus antigen and hepatitis E virus antigen, or from other viral pathogens, such as paramyxoviruses: Respiratory Syncytial virus (such as F and G proteins or derivatives thereof), or antigens from parainfluenza virus, measles virus, mumps virus, human papilloma viruses (for example HPV6, 11, 16, 18; e.g. L1, L2, E1, E2, E3, E4, E5, E6, E7 proteins), flaviviruses (e.g. Yellow Fever Virus, Dengue Virus, Tick-borne encephalitis virus, Japanese Encephalitis Virus) or Influenza virus cells such as HA, NP, NA, or M proteins, or combinations thereof), or antigens derived from bacterial pathogens such as *Neisseria* spp, including *N. gonorrhea* and *N. meningitidis* (e.g., transferrin-binding proteins, lactoferrin binding proteins, PilC, adhesins); *S. pyogenes* (for example M proteins or fragments thereof, C5A protease), *S. agalactiae, S. mutans*; H. ducreyi; *Moraxella* spp, including *M. catarrhalis*, also known as Branhamella catarrhalis (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), B. parapertussis and *B. bronchiseptica*; *Mycobacterium* spp., including *M. tuberculosis* (for example ESAT6, Antigen 85A, -B or -C, MPT 44, MPT59, MPT45, HSP10, HSP65, HSP70, HSP 75, HSP90, PPD 19 kDa [Rv3763], PPD 38 kDa [Rv0934]), *M. bovis, M. leprae, M. avium, M. paratuberculosis, M. smegmatis; Legionella* spp, including *L. pneunophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi*, S. choleraesuis, *S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example *botulinum* toxin and derivative thereof), *C. difficile* (for example *clostridium* toxins A or B and derivatives thereof); *Bacillus* spp., including *B. anthracis; Cornebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Ricketsia* spp, including *R. rickettsii; Chlamydia* spp., including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamnoeba* spp., including *E. histolytica; Babesia* spp., including *B. microti; Trypanosoma* spp., including *T. cruzi; Giardia* spp., including *G. lamblia; Leshmania* spp., including *L. major; Pneunocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans.*

In some embodiments, two or more antigens may be used in the immunization methods and kits of the invention. In the priming preparations and the boosting preparations having a nucleic acid component, the two or more antigens may be fusion proteins, in which either the full-length antigenic proteins or immunogenic fragments thereof are expressed from a single open-reading frame (e.g. expressed as a single transcript). In other embodiments, the two or more antigens may be expressed from different open-reading frames (e.g. expressed as separate transcripts) under the control of a single promoter or different promoters. In the boosting preparations, the two or more antigens may be present as a mixture of antigens or as one or more fusion proteins. The two or more antigens may be from a single pathogen or multiple pathogens.

Other preferred specific antigens for *M. tuberculosis* are for example Rv2557, Rv2558, RPFs: Rv0837c, Rv1884c, Rv2389c, Rv2450, Rv1009, aceA (Rv0467), PstS1, (Rv0932), SodA (Rv3846), Rv2031c 16 kDal., Tb Ral2, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd 14-DPV-MTI, DPV-MTI-MSL, Erd 14-DPV-MTI-MSL-mTCC2, Erd14-DPV-MTI-MSL, DPV-MTI-MSL-mTCC2, TbH9-DPV-MTI (WO 99/51748). Most preferred antigens for *Chlamydia* include for example the High Molecular Weight Protein (HWMP) (WO 99/17741), ORF3 (EP 366 412), and putative membrane proteins (Pmps). Other *Chlamydia* antigens of the vaccine formulation can be selected from the group described in WO 99/28475.

Preferred bacterial vaccines comprise antigens derived from *Streptococcus* spp, including *S. pneumoniae* (PsaA, PspA, streptolysin, choline-binding proteins) and the protein antigen Pneumolysin (Biochem Biophys Acta, 1989, 67, 1007; Rubins et al., Microbial Pathogenesis. 25, 337-342), and mutant detoxified derivatives thereof (WO 90/06951; WO 99/03884). Other preferred bacterial vaccines comprise antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843, 464) or multiple copy variants or fusion proteins thereof.

The antigens that may be used in the present invention may further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp.

Vaccines of the present invention may also be used for the prophylaxis or therapy of chronic disorders in addition to allergy or infectious diseases. Such chronic disorders are diseases such as asthma, atherosclerosis, and Alzheimers and other autoimmune disorders. Vaccines for use as a contraceptive are also contemplated.

Antigens relevant for the prophylaxis and the therapy of patients susceptible to or suffering from Alzheimer neurodegenerative disease are, in particular, the N terminal 39-43 amino acid fragment (Aβ, the amyloid precursor protein and smaller fragments. This antigen is disclosed in the International Patent Application No. WO 99/27944—(Athena Neurosciences).

Potential self-antigens that could be included as vaccines for auto-immune disorders or as a contraceptive vaccine include: cytokines, hormones, growth factors or extracellular proteins, more preferably a 4-helical cytokine, most preferably IL13. Cytokines include, for example, IL1, IL2, IL3, IL4, IL5, IL6, IL7, IL8, IL9, IL10, IL1 1, IL2, IL13, IL14, IL15, IL16, IL17, IL18, IL20, IL21, TNF, TGF, GMCSF, MCSF and OSM. 4-helical cytokines include IL2, IL3, IL4, IL5, IL13, GMCSF and MCSF. Hormones include, for example, luteinising hormone (LH), follicle stimulating hormone (FSH), chorionic gonadotropin (CG), VGF, GHrelin, agouti, agouti related protein and neuropeptide Y. Growth factors include, for example, VEGF.

The nucleic acids used in the priming preparation or boosting preparations may be RNA or DNA including genomic DNA, synthetic DNA or cDNA. Preferably the nucleotide sequence is a DNA sequence and most preferably, a cDNA sequence. In order to obtain expression of the antigenic peptide within mammalian cells, it is necessary for the nucleotide sequence encoding the antigenic peptide to be presented in an appropriate vector system. By "appropriate vector" as used herein is meant any vector that will enable the antigenic peptide to be expressed within a mammal in sufficient quantities to evoke an immune response.

For example, the vector selected may be a plasmid, a phagemid or a viral vector. The vector may comprise promoter and polyadenylation/transcriptional termination sequences arranged in the correct order to obtain expression of the antigenic peptides. In one embodiment, the vector is a plasmid (e.g. pDNAVACC). The construction of vectors which include these components and optionally other components such as enhancers, restriction enzyme sites and selection genes, such as antibiotic resistance genes, is well known to persons skilled in the art and is explained in detail in Maniatis et al "Molecular Cloning: A Laboratory Manual", Cold Spring Harbour Laboratory, Cold Spring Harbour Press, Vols 1-3, 2-nd Edition, 1989.

In certain embodiments, the nucleic acid in the priming preparation or boosting preparations with a nucleic acid component is a vector encoding an HSV-2 antigen under the control of a promoter. As used herein, "under the control of" or "operably linked" means that the promoter is in the correct location and orientation in relation to a polynucleotide encoding the antigen to control the initiation of transcription by RNA polymerase and expression of the polynucleotide. Suitable promoters for use in the vector include, but are not limited to, human cytomegalovirus (CM V) immediate early gene promoter, the SV40 early promoter, the Rous sarcoma virus long terminal repeat, RNA pol I, pol II, and pol III promoters. In certain embodiments, the promoter is a CMV promoter, preferably a CMV immediate early gene promoter. The sequence encoding the HSV-2 antigen can be codon-optimized for expression in mammalian cells, such as human cells. In certain embodiments, the vector encodes a full-length, human codon-optimized gD glycoprotein. In one embodiment, the full-length gD glycoprotein human codon-optimized sequence comprises a sequence of SEQ ID NO: 1.

A vector carrying nucleic acids encoding an antigenic peptide can be administered in a variety of manners. It is possible for the vector to be administered in a naked form (that is as naked nucleotide sequence not in association with liposomal formulations, with viral vectors or transfection facilitating proteins) suspended in an appropriate medium, for example a buffered saline solution such as PBS and then injected intramuscularly, subcutaneously, intradermally or mucosally or administered using gene gun or other electronic (i.e., electroporation) devices. It is additionally possible for the vectors to be encapsulated by, for example, liposomes or within polylactide co-glycolide (PLG) particles for administration via the nasal or pulmonary routes. In preferred embodiments, the vector carrying nucleic acids encoding an HSV-2 antigen is administered in a naked form via an intramuscular route.

It is also possible, according to one embodiment of the invention, for intradermal administration of the vector, preferably via use of gene-gun (particularly particle bombardment) administration techniques. Such techniques may involve coating of the vector on to gold beads which are then administered under high pressure into the epidermis, such as, for example, as described in Haynes et al. J. Biotechnology 44: 37-42 (1996).

Recombinant viral vectors can also be used to deliver DNA antigens. Advantages to this approach include abundant expression of DNA-encoded proteins in multiple cell types, strong enhancement of CTL responses and the ability of the virus to encode multiple genes. Vaccinia virus (including modified virus Ankara) and adenovirus (non-replicating) are two popular viruses used for vaccine development (Im and Hanke, Expert, Rev. Vaccines 3:S89-S97 (2004); Basak et al., Viral Immunol. 17:182-196 (2004)).

Recent modifications of DNA vaccines include the development of minigenes encoding single CTL epitopes, the use of gene-encoded targeting signals to allow more efficient presentation of epitopes by the MHC-pathway and the generation of secreted proteins to target MHC class II pathway (Doria-Rose and Haigwood, Methods 31:207-216 (2003); Leifert et al., Immunol. Rev. 199:40-53 (2004)).

In certain embodiments, the boosting preparations comprise the protein antigen encapsulated in liposomes. The antigen in the boosting preparations is, in some embodiments, the same antigen encoded by the nucleic acid in the priming preparation and boosting preparations having a nucleic acid component. In one embodiment, the boosting preparations comprise an HSV-2 antigen encapsulated in liposomes. In another embodiment, the HSV-2 antigen is a gD glycoprotein. The gD glycoprotein may be the full-length glycoprotein or an immunogenic fragment thereof. For instance, in certain embodiments, the antigen encapsulated in liposomes in the boost preparations (e.g., first and second boosting preparations) is the extracellular domain of gD comprising amino acids 1-314 of gD protein. In other embodiments, the antigen is the extracellular domain of gD comprising the amino acid sequence of SEQ ID NO: 2.

Liposomes have several potential advantages as delivery platforms for vaccines. Encapsulation of antigens within liposomes sequesters these antigens, thus the liposomes serve as an antigen depot capable of sustained antigen release. In addition, liposomes are biocompatible and biodegradable, and low in toxicity and immunogenicity. When appropriately sized (e.g., >0.2 µm up to 5 µm), liposomes are selectively taken up by antigen-presenting cells in the body, and have the potential to induce both humoral antibody and CTL responses. Liposomes serve as antigen carrier/vehicle as well as being an adjuvant that can be administered repeatedly without toxicity or immunogenicity.

Liposomes are structures consisting of a membrane bilayer composed of phospholipids of biological or synthetic origin, usually spherical in shape. Liposomes form naturally when phospholipids or lipids contact water. The structure of liposomes can be manipulated by methods to form them in the laboratory, including the input of energy in the form of heat, sonic energy, freeze-thaw cycles, or shear forces. The phospholipid bilayer membrane of liposomes separates and protects entrapped materials in the inner aqueous core from the outside. Both water-soluble and -insoluble substances can be entrapped in different compartments, the aqueous core and bilayer membrane, respectively, of the same liposome. Chemical and physical interaction of these substances can be eliminated because the substances are in these different compartments.

Liposomes used with the methods and kits of the present invention can be prepared using any methods known in the art. These liposomes may have an average diameter of about 0.5 to 5 microns, about 2 to 4 microns, or about 1 to 4 microns. In some instances, liposomes of about 0.2 to 8 microns may also be useful. In certain embodiments, liposomes that may be used in the methods and kits of the invention are anionic liposomes (e.g. negatively-charged). The charge of the liposomes can be manipulated by incorporating ionic lipids. See, e.g., U.S. Pat. No. 5,290,563, which is hereby incorporated by reference. For instance, incorporation of dicetyl phosphate confers a negative charge to liposomes. In one embodiment, the liposomes used in the boost preparations are anionic liposomes comprising phosphatidylcholine, cholesterol, and dicetyl phosphate. In another embodiment, the liposomes comprise phosphatidylcholine, cholesterol, and dicetyl phosphate in a ratio of 7:3:0.5 mole %. In some embodiments, the liposomes used in the boost preparations consist of lipids, i.e. the liposomes do not contain additional proteins, ligands, or adjuvants. For instance, in one embodiment, the liposomes are non-fusogenic liposomes (i.e. do not contain any proteins, such as viral proteins incorporated into the liposomal membrane).

By way of example, one method for making the liposomes that can be used in the boosting preparations in the methods and kits of the invention is described as follows. Liposomes of the subject invention are prepared at the following lipid concentrations:

Phosphatidylcholine/cholesterol/dicetyl phosphate 7/3/0.5 mole %. Dicetyl phosphate is dissolved in chloroform plus 5% of ethanol, sonicated and phosphatidylcholine and cholesterol are then added. Lipids are dried in a Labconco rotary evaporator for one hour and traces of chloroform are removed by freeze-drying with a Freezone 4.5 Freeze Dry System overnight. The lipid film is hydrated with antigen, such as gD glycoprotein from HSV-2 (gD), at a concentration of 125-300 µg/ml in 10 mM HEPES-buffer, 150 mM NaCl, pH 7.4 (HBS), and filtered with a 0.2 µm nylon filter. The mixture is vortexed thoroughly and allowed to sit for 1 hour and then vortexed again to ensure the formation of multilamellar vesicles. The resultant liposomes are then subjected to three cycles of freeze-and-thaw (1 cycle=freezing for one hour and thawing for one hour at room temperature). The size of the liposomes is measured with a N4 MD Submicron Particle Size Analyzer (Coulter Electronics). The zeta-potential was measured using Zeta-Puls zeta-potential analyzer (Brookhaven Instruments) in 5 mM HEPES buffer, 1.0 mM NaCl, pH 7.4. To obtain liposomes with specific average diameters less than 2 microns, after the third freeze-thaw cycle, liposomes can be warmed in a water bath to 50° C. and extruded through a polycarbonate filter with a pore size of 1.0 µm to obtain liposomes with average diameters of about 1.0 µm. The liposomes can be further extruded to obtain small sized liposomes, for example, by further extruding the liposomes through a polycarbonate filter with pore size of 0.4 µm and finally 0.2 µm using a hand-held Avanti micro-extruder to obtain liposomes with average diameters of about 0.2 µm.

In certain embodiments, liposomes that may be used in the methods and kits of the invention are "long circulating liposomes" (a.k.a. "sterically stabilized liposomes"), which are liposomes that comprise one or more specialized lipids that, when incorporated into liposomes, result in enhanced circulation lifetimes relative to liposomes lacking such specialized lipids. Examples of long circulating liposomes known in the art include those in which the liposome (A) comprises one or more glycolipids such as monosialoganglioside GM1 or (B) comprises one or more lipids derivatized with one or more hydrophilic polymers, such as a polyethylene glycol (PEG) moiety. While not wishing to be bound by any theory, at least for long circulating liposomes containing gangliosides, sphingomyelin, or PEG-derivatized lipids, the enhanced circulation half-life of these liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside GM1, galactocerebroside sulfate and phosphatidylinositol to improve blood half-lives of liposomes. These findings were expounded upon by Gabizon et al. (Proc. Natl. Acad. Sci. USA, 1988, 85, 6949). U.S. Pat. No. 4,837,028 and published PCT application WO 88/04924, both to Allen et al., disclose liposomes comprising (1) sphingomyelin and (2) the ganglioside GM1 or a galactocerebroside sulfate ester. U.S. Pat. No. 5,543,152 (to Webb et al.) discloses liposomes comprising sphingomyelin. Liposomes comprising 1,2-sn-dimyristoylphosphatidylcholine are disclosed in published PCT application WO 97/13499 (to Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contain a PEG moiety. Ilium et al. (FEBS Letters, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) and liposomes comprising such phospholipids are described by Sears (U.S. Pat. Nos. 4,426,330 and 4,534,899). Klibanov et al. (FEBS Letts., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the chemical attachment of PEG to DSPE (distearoylphosphatidylethanolamine).

Liposomes having covalently bound PEG moieties on their external surface are described in European Patent No. 0 445 131 B1 and published PCT application WO 90/04384 to Fisher. Liposome compositions containing 1-20 mole percent (mol %) of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in published PCT application WO 91/05545 and U.S. Pat. No. 5,225,212 (both to Martin et al.) and in published PCT application WO 94/20073 (Zalipsky et al.) Liposomes comprising PEG-modified ceramide lipids are described in published PCT application WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized on their surfaces with functional moieties.

Various liposomes comprising dimyristoylphosphatidylglycerol (DMPG) have been described. Generally, however, such liposomes comprise DMPG in a mol % of about 10% or higher (see, for example, Akhtar et al. (Nucl. Acids Res., 1991, 19, 5551; Yachi et al. (Biopharm. Drug Dispos., 1996, 17, 699; and Farmer et al. (Meth. Enz., 1987, 149, 184). Liposomes having 3 mol % DMPG have been described, but such liposomes included a component (in particular, a phosphatidylcholine derivative) that is not found in the liposomal compositions of the present invention. Such phosphatidylcholine derivative components include, e.g., 10 mol % distearoylphosphatidylcholine (DSPC) (Brodt et al., Cancer Immunol. Immunother., 1989, 28, 54) or 7 mol % dimyristoylphosphatidylcholine (DMPC) (Perez-Soler et al., J. Nuclear Med., 1985, 26, 743; Wasan et al., Antimicrobial Agents and Chemotherapy, 1993, 37, 246; and Li et al., Oncology Res., 1995, 7, 611).

The liposome preparation may either be freshly prepared or lyophilized for long term storage. Both preparations can be used with comparable effectiveness. The liposomes used in the methods of the invention can be all the same (e.g. same compositions or same size), or include more than one type of liposome.

In certain embodiments, commercially available liposomes can be used. For example, liposomes can be made under contract by Northern Lipids Inc. (Vancouver, BC), a Contract Research Organization that specializes in the development of lipid-based liposome formulations.

In certain other embodiments, liposomes of various sizes can be prepared using the methodology as described below. The resulting liposomes, depending on specific preparation protocols, are typically sized between about 0.5 µm and 5 µm, for example, at 4 µm, 1 µm, or 0.2 µm by passing preparations through a microfluidizer. Briefly, negatively-charged liposomes can be prepared at the following lipid concentrations: Phosphatidylcholine/cholesterol/dicetyl phosphate 7/3/0.5 mole %. Antigen such as HSV-2 antigen (e.g. gD glycoprotein of HSV-2) is incorporated into multilaminar liposomes at several concentrations for the testing of immune responses. Liposome size can be measured with a N4 MC Submicron Particle Size Analyzer (Coulter Electronics). In certain embodiments, antigen preparations can be lyophilized for storage and then reconstituted before use. Both size and ζ-potential (zeta, a measure of charge) might be measured before use. The ζ-potential can be determined using Zeta-Puls ζ-potential analyzer (Brookhaven Instruments). The lipid:antigen protein ratio can be varied in some preparations in order to determine the importance of this ratio on immune responses to the specific antigen (e.g., gD of HSV-2).

The priming and boosting preparations are administered in such amount as will be prophylactically or therapeutically effective. The exact quantity may vary considerably depending on the species and weight of the animal being immunized, the route of administration, the potency and dose of the priming and boosting preparations, the nature of the disease state being treated or protected against, the capacity of the subject's immune system to produce an immune response and the degree of protection or therapeutic efficacy desired. Based upon these variables, a medical or veterinary practitioner will readily be able to determine the appropriate dosage level. In the following example, suitable doses of the DNA vector encoding gD glycoprotein from HSV-2 used in the priming preparation and secondary boosting preparation were determined to be about 50 µg to 100 µg for guinea pigs. These doses can be scaled to appropriate doses for use in humans by one of ordinary skill in the art without undue experimentation. For instance, suitable doses of the DNA vector encoding HSV-2 gD protein for use in humans may be from about 0.5 mg to about 10 mg, or about 1 mg to about 5 mg. The precise dosage will depend on the type of vector used, the promoter, the level of expression of antigen, administration methods, and the type and level of codon-optimization of the antigen nucleotide sequence. In the following example, a suitable dose of liposomal-encapsulated HSV-2 gD glycoprotein used in the boosting preparations was determined to be about 30 µg/100 µlfor guinea pigs. Similar to the doses of DNA vector, these doses for the boosting preparation can be adjusted appropriately for use in humans. Suitable human doses for the liposomal-encapsulated gD antigen may be about 3 to 6 µg/100 to 400 µl, for instance about 3 µg/100 µl to about 6 µg/100 µl.

The methods and kits according to the present invention can be used in relation to prophylactic or treatment procedures of all animals including, for example, domestic animals, laboratory animals, farm animals, captive wild animals and, most preferably, humans.

It is contemplated that the methods and kits of the invention can also be practiced with the addition of one or more adjuvants known in the art. However, in some embodiments, no additional adjuvant is included in the boosting preparations. The inventors have discovered that the novel methods provided herein achieve the desired immune responses without the need for any adjuvant other than liposome, thus avoiding risks and complications associated with many adjuvants, especially the bacterial toxins such as cholera toxin (CT) and the E. coli heat labile enterotoxin (LT).

An adjuvant is a substance or procedure which augments specific immune responses to antigens by modulating the activity of immune cells. Exemplary adjuvants include salt based adjuvants such as alum salts, bacterial-derived adjuvants like lipopolysaccharides and bacterial toxins, adjuvant emulsions that enable the slow release of antigen, agonistic antibodies to co-stimulatory molecules, Freunds adjuvant, muramyl dipeptides, and recombinant/synthetic adjuvants. In one particular embodiment, the adjuvant is a toll-like receptor (TLR) ligand, particularly a TLR-4, such as monophosphoryl lipid A (MPL), or TLR-7 ligand, such as R837. Recently, TLR-4 and TLR-7 ligands in combination with a nanoparticle formulation have been reported to enhance and prolong antibody responses when administered with antigen following immunization (Kasturi et al. (2011) Nature, Vol. 470: 543-560). Thus, TLR-4 and/or TLR-7 ligands can be included in the priming and/or boosting preparations of the invention. Alum is the most common salt-based adjuvant used to stimulate immune responses to protein vaccines and is the only adjuvant approved for human use in the United States (Alving, Vaccine 20(3):S56-S64 (2002); Hunter, Vaccine 20(3):S7-12 (2002)). However, alum favors Th2-biased responses and does not stimulate cell-mediated immunity. Mucosal immunity can be induced through the use of bacterial toxins such as cholera toxin (CT) and the E. coli heat labile enterotoxin (LT), however the safety of these adjuvants is questionable (Alving, Vaccine 20(3):S56-S64 (2002); Hunter, Vaccine 20(3):S7-12 (2002)). The development of newer, safer adjuvants has recently focused on stimulating particular immune response pathways. Co-administration of cytokines, such as interferon-γ and granulocyte-macrophage colony stimulating factor (GM-CSF), has shown promise in stimulating cellular immune responses (reviewed in (Petrovsky and Aguilar, Immunol. Cell Biol. 82:488-496 (2004)). High levels of cytokines can cause toxicity however, and dosing regimens must be carefully modulated. Administration of cytokines has particular promise for DNA vaccination where genes encoding both the cytokine and antigen could be simultaneously expressed by the same vector. Additional adjuvants being explored include those that target the toll signaling pathway. CpG DNA motifs commonly found in bacterial DNA are potent activators of cellular immune responses, and newer generation DNA-based vaccines often encode multiple CpG motifs (reviewed in (Petrovsky and Aguilar, Immunol. Cell Biol. 82:488-496 (2004)).

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

Efficacy of a Mucosal Herpes Simples Virus Type-2 Vaccine in Virally-Infected Guinea Pigs Previously, we showed that a mucosal HSV-2 vaccine significantly reduced the recurrence of genital herpes in HSV-2 virus-infected guinea pigs, thereby demonstrating the therapeutic efficacy of the vaccine. See U.S. Patent Publication No. 2012/0027841A 1, which is hereby incorporated by reference in its entirety. In this example, we compared the therapeutic efficacy of the mucosal HSV-2 vaccine (i.e. BRM vaccine), which is comprised of an intramuscularly administered DNA vector encoding HSV-2 gD antigen and an intranasally administered liposomal-encapsulated gD protein antigen, with a HSV-2 gD subunit vaccine comprising Alum and MPL in guinea pigs four weeks post an established HSV-2 infection. The guinea pig model is one of the most widely used animal models for studying genital herpes (Stanberry et al. (1985) Intervirology, Vol. 24(4): 226-231; Stanberry et al. (1982) J Infect Dis, Vol. 146(3): 397-404). Similar to humans, the guinea pig model features an initial acute infection with severe genital lesions followed by spontaneous recurrent events, and has been widely used for the evaluation of both prophylactic and therapeutic vaccines.

Previously, we successfully established latency of HSV-2 infection in naïve Dunkin-Hartley guinea pigs by dosing the MS strain at three different infection doses ($1 \times 10^6$, $2 \times 10^5$ and $2 \times 10^4$ pfu/animal). A dose of $2 \times 10^5$ pfu HSV-2/animal led to less animal death, and therefore this infection dose was selected to establish the HSV-2 infection in the animals for this study. Guinea pigs were inoculated with a dose of 2×10$^5$ pfu HSV-2/animal (strain MS) intravaginally. Clinical signs of disease and morbidity were monitored daily post infection. Clinical signs were scored according to the following scale: 0=no clinical signs of disease (no visible redness or lesions), 1=vaginal erythema (redness or mild swelling), 2=single or few modest herpetic lesions (erosions, vesicles, or moderate swelling), 3=several large or fused vesicles, 4=large ulcers with severe maceration and/or urinary retention and/or hind limb paralysis, 5=found dead. Animals that reached a clinical score of 4 were immediately euthanized. Vaginal swabs collected on day 2, day 4, and day 21 post infection were analyzed by plaque assay to confirm if viral infection and replication successfully occurred in the vaginal cavity. The successfully infected guinea pigs displayed clinical signs of disease ranging from a clinical score of 2-3 during the acute phase, and were randomly divided into three treatment groups (n=10-12/group) on day 28 post infection. There was no significant difference among the three groups in the rate of recurrences (appearance of lesions) prior to treatment (FIG. 1).

Figure 2:
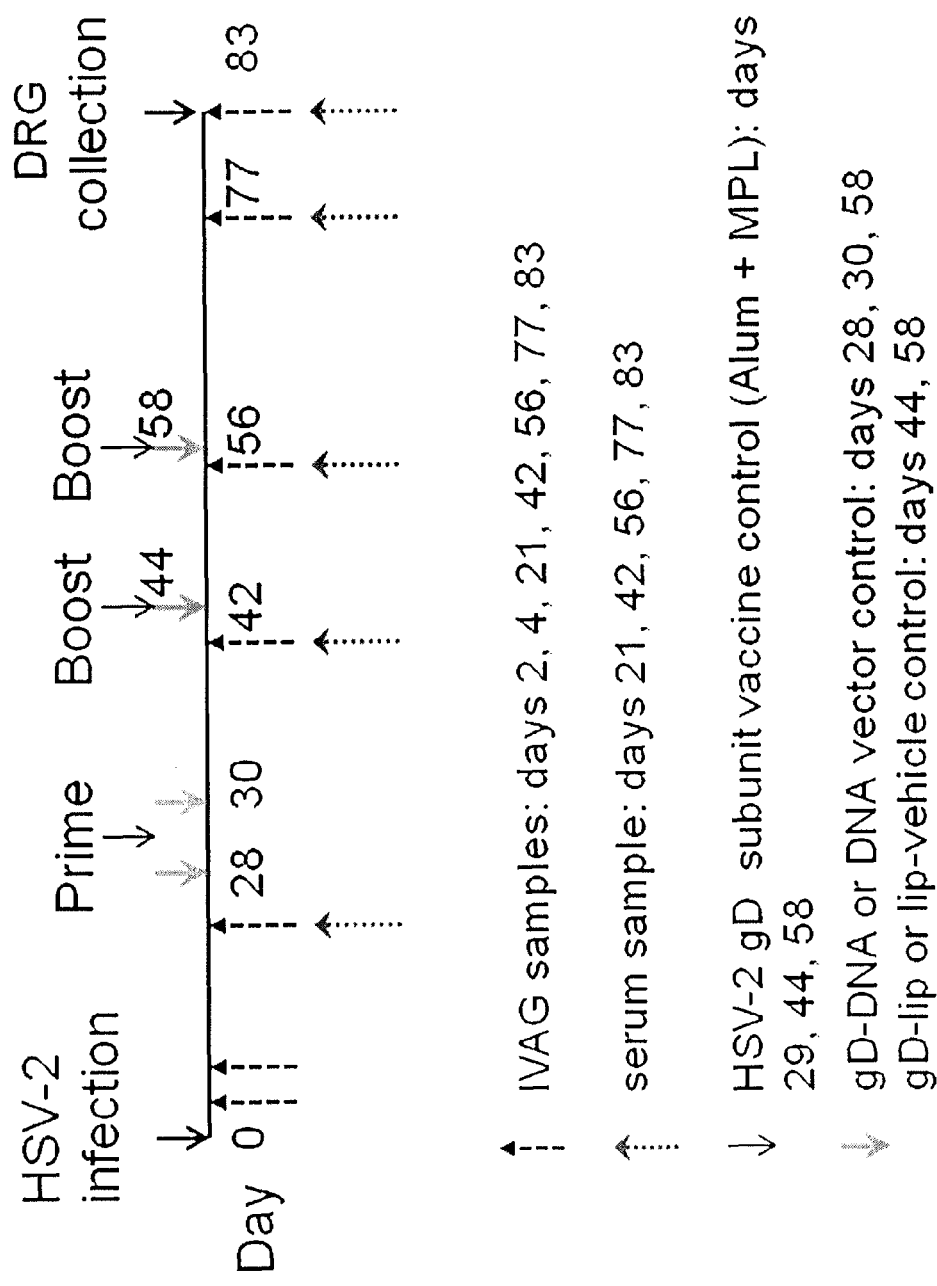
FIG. 2. Schematic showing immunization protocol and same collection schedule in three treatment groups (BRM vaccine, vehicle control, HSV-2 subunit vaccine) of HSV-2 infected guinea pigs. Four weeks post intravaginal infection with HSV-2, a gD-DNA vector prime (BRM vaccine group) or vector control (control group) was injected intramuscularly over two days (28 and 30). Two weeks later an intranasal gD-liposome boost (BRM vaccine group) or empty liposome (control group) was administered. Two weeks after the first boost, a second boost of i.m. gD-DNA and i.n. gD-liposomes (BRM vaccine group) or vector and empty liposomes (control group) was administered. In the HSV-2 subunit vaccine group, the HSV-2 gD vaccine was administered subcutaneously on days 29 (prime), 44 (first boost), and 58 (second boost) after HSV-2 infection. Serum samples were collected on days 21, 42, 56, 77, and 83; vaginal swab samples were collected on days 2, 4, 21, 42, 56, 77, and 83; dorsal root ganglia were harvested at the end of the study to determine the latent HSV-2 DNA copy numbers.

Each of the three treatment groups were immunized with one of the following: the mucosal vaccine (BRM vaccine), the HSV-2 gD subunit vaccine (reference vaccine), or vehicle control as indicated in the following table and the schematic in FIG. 2.

| Group | Day 28 | Day 29 | Day 30 | Day 44 | Day 58 |
| --- | --- | --- | --- | --- | --- |
| BRM vaccine (n = 12) | gD-DNA (i.m.) | NA | gD-DNA (i.m.) | gD-lip (i.n.) | gD-DNA (i.m.) + gD-lip (i.n.) |
| Vehicle control (n = 10) | DNA vector (i.m.) | NA | DNA vector (i.m.) | Lip vehicle (i.n.) | DNA vector (i.m.) + Lip vehicle (i.n.) |
| Reference vaccine (n = 12) | NA | HSV-2 gD (s.c.) | NA | HSV-2 gD (s.c.) | HSV-2 gD (s.c.) |

The prime (gD-DNA) in the mucosal vaccine was a DNA plasmid vector encoding a codon-optimized, full-length gD glycoprotein gene under the control of a cytomegalovirus immediate early promoter and was administered intramuscularly on Days 28 and 30 post-infection (total 100 μg DNA per guinea pig; 50 μg per animal per day) in the BRM vaccine group. The gD-DNA vector was intramuscularly administered again on day 58 post-infection (2×50 μg/200 ul/leg; total 100 μg DNA per guinea pig) as part of a second boost preparation. The plasmid without the gD gene (DNA vector) was administered to animals in the vehicle control group at the same dose, frequency, and route as the gD-DNA vector.

The boost preparation (gD-lip) in the mucosal vaccine was a preparation of negatively-charged liposomes encapsulating the extracellular domain (amino acids 1-314) of the gD glycoprotein and was administered intranasally on Days 44 and 58 post-infection (30 μg/100 μl/animal, 50 μl/nostril) in the BRM vaccine group. A preparation of empty negatively-charged liposomes (Lip vehicle) was administered to animals in the vehicle control group at the same dose, frequency, and route as the gD-lip preparation.

Each dose of the reference vaccine (HSV-2 gD subunit vaccine) comprised 5 μg of the extracellular domain (amino acids 1-306) of the gD glycoprotein, 125 μg Alum (Alhydrogel), and 12.5 μg monophosphoryl lipid A (MPL). The HSV-2 gD subunit vaccine was administered subcutaneously on days 29, 44, and 58 post-infection to animals in the reference vaccine group.

Figure 3:
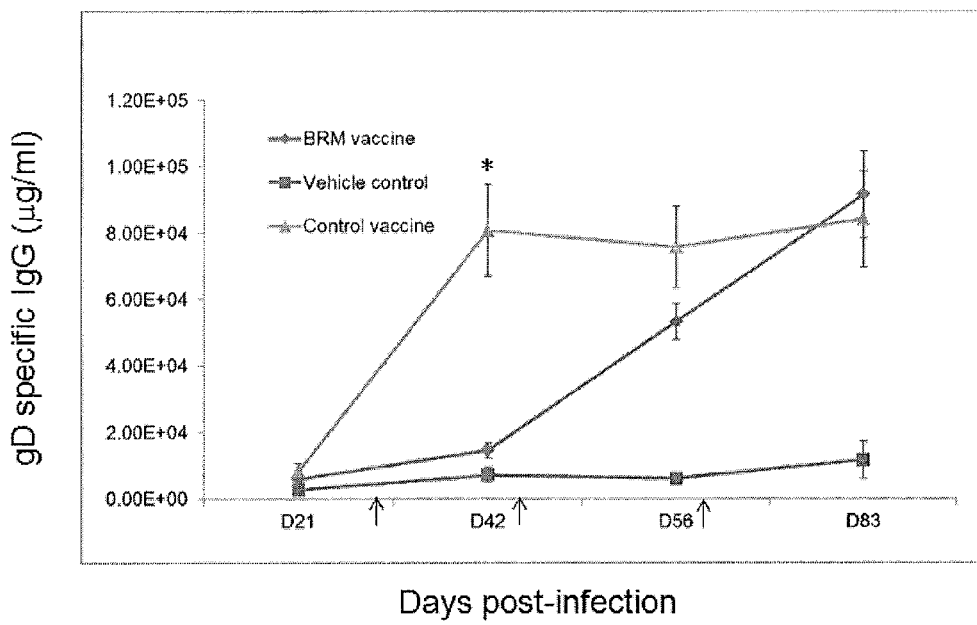
FIG. 3. A. Antigen-specific (HSV-2 gD) serum IgG in unvaccinated guinea pigs (vehicle control) or guinea pigs vaccinated either with the mucosal vaccine (BRM vaccine) or an HSV-2 gD subunit vaccine (control vaccine). The arrow indicates the days when immunizations were received. Asterisk=$p<0.05$. B. Antigen-specific (HSV-2 gD) vaginal IgG at day 83 post-HSV-2 infection in unvaccinated guinea pigs (vehicle control; n=9) or guinea pigs vaccinated either with the mucosal vaccine (BRM vaccine; n=11) or an HSV-2 gD subunit vaccine (reference vaccine; n=12).
Figure 3:
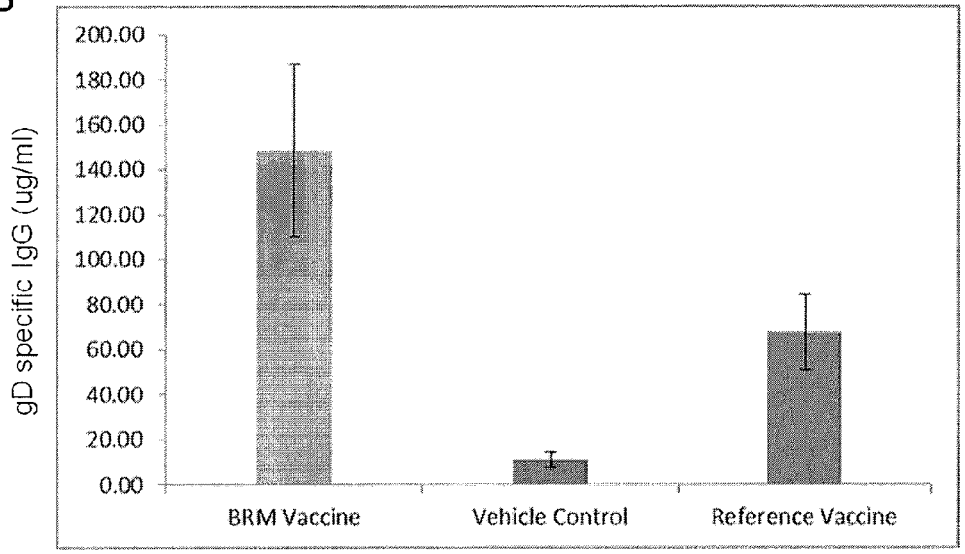
Figure 4:
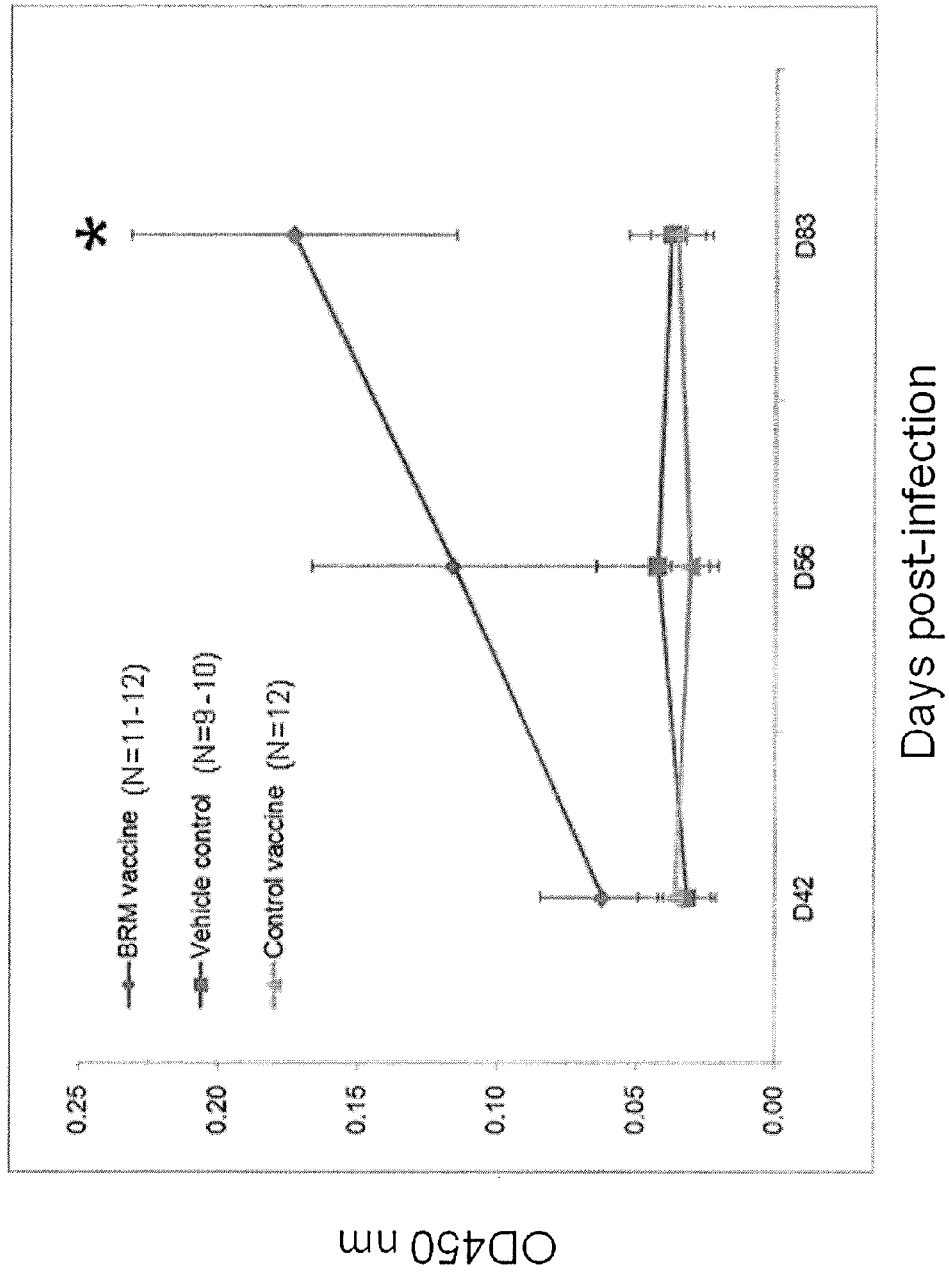
FIG. 4. Antigen-specific (HSV-2 gD) vaginal IgA in unvaccinated guinea pigs (vehicle control) or guinea pigs vaccinated either with the mucosal vaccine (BRM vaccine) or an HSV-2 gD subunit vaccine (control vaccine). Asterisk=$p<0.05$.

Serum and vaginal swab samples were collected from the vaccinated and unvaccinated groups of guinea pigs on day 21 three weeks after infection (7 days before prime), day 42 (immediately before first boost), day 56 (immediately before second boost), and on day 83 (end of study). The samples were analyzed by ELISA to assess serum and vaginal antibody responses. Antigen-specific (HSV-2 gD) IgG antibody serum responses for each of the three treatment groups are shown in FIG. 3A. The results show that the reference HSV-2 subunit vaccine induced a rapid increase in serum antigen-specific IgG, whereas the mucosal vaccine (BRM vaccine) produced a more gradual increase in serum antigen-specific IgG levels. However, the mucosal vaccine induced an approximate 10-fold increase in anti-HSV-2 gD vaginal IgG antibodies as compared to the vehicle control group at day 83 post-infection, whereas the HSV-2 subunit vaccine induced a more moderate increase (FIG. 3B). Importantly, only the mucosal vaccine induced a significant increase in antigen-specific vaginal IgA antibodies (FIG. 4). No increase in vaginal IgA was observed in unvaccinated animals or animals vaccinated with the subunit vaccine.

Figure 5:
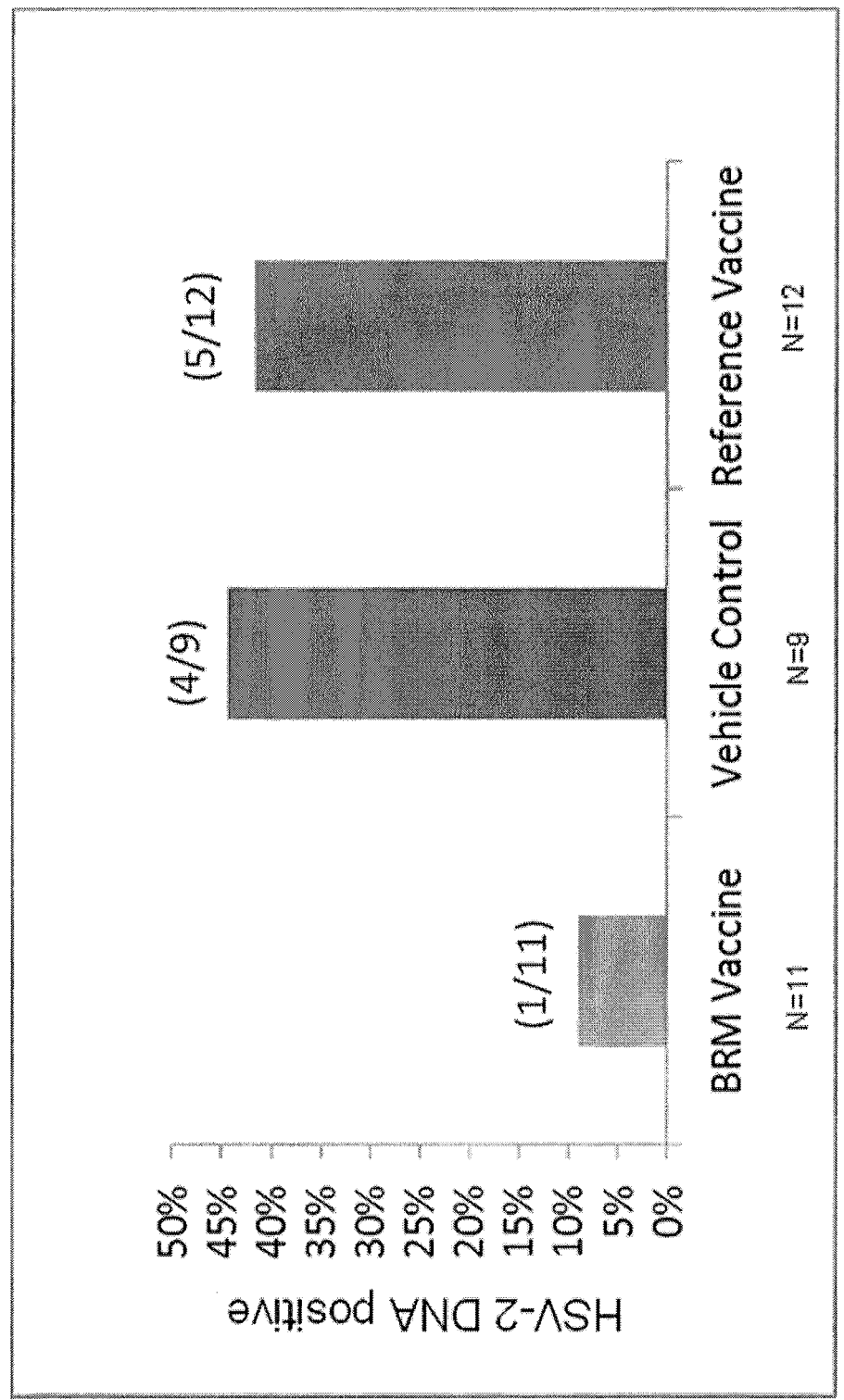
FIG. 5. Detection of vaginal HSV-2 DNA copies by real-time qPCR at day 83 post-infection in unvaccinated guinea pigs (vehicle control; n=9) or guinea pigs vaccinated either with the mucosal vaccine (BRM vaccine; n=11) or an HSV-2 gD subunit vaccine (reference vaccine; n=12). Samples were deemed positive if they contained greater than 5 copies of HSV-2 DNA.

Viral shedding was assessed by RT-PCR for HSV-2 DNA copies of vaginal swab samples. FIG. 5 shows the percentage of samples from each treatment group that were positive (greater than 5 copies of HSV-2 DNA) for HSV-2 DNA at day 83 post-infection. Animals that received the mucosal vaccine (BRM vaccine) had a significantly lower percentage of vaginal samples that were positive for the virus as compared to unvaccinated animals or animals that received the subunit reference vaccine, indicating that the mucosal vaccine substantially reduced the amount of vaginal viral shedding. The strong mucosal antibody responses induced by the BRM vaccine may contribute to the observed reduction in viral shedding with this vaccine.

Figure 6:
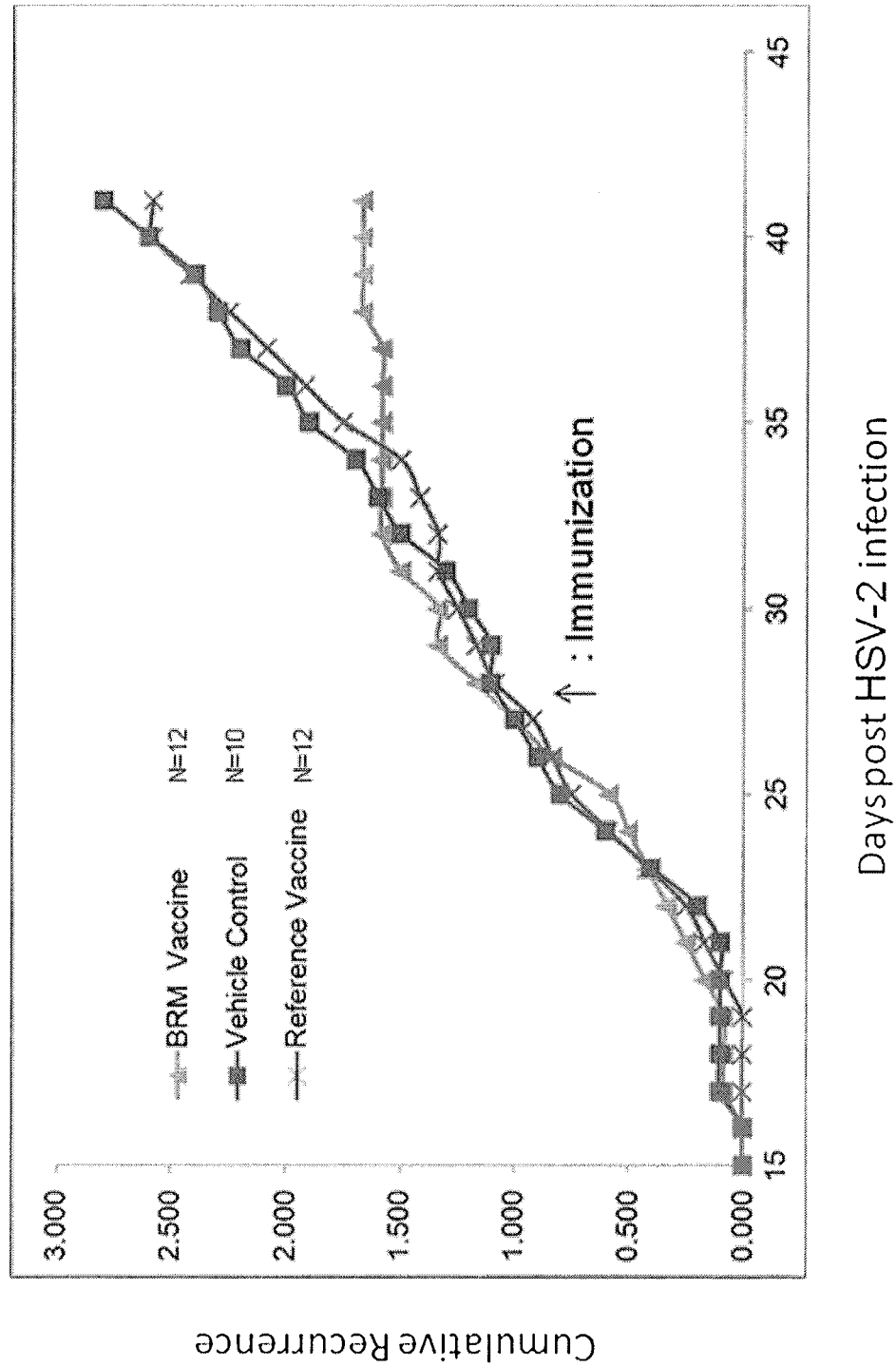
FIG. 6. Cumulative recurrence per animal per group in unvaccinated guinea pigs (vehicle control) or guinea pigs vaccinated either with the mucosal vaccine (BRM vaccine) or an HSV-2 gD subunit vaccine (reference vaccine) from day 15 to day 42 post-infection with HSV-2. Animals were observed for evidence of spontaneous recurrent herpatic lesions and recurrent episodes were enumerated as cumulative recurrences (appearance of lesions) per guinea pig for each group, adjusted for the number of days the recurrences were observed. The arrow indicates the day when the priming dose in the vaccine groups was administered.

After the primary infection, HSV-2 sets up a latent infection in the sacral nerve ganglia and reactivation of virus occurs periodically over the lifetime of an individual and may result in recurrent disease or unapparent virus shedding that occurs even in the presence of immune responses to the initial virus infection (Whitley and Roizman (2001) Lancet, Vol. 357(9267): 1513-1518). A successful therapeutic vaccine would have to prevent or markedly reduce periodic recurrences. After immunization of infected guinea pigs, the animals were observed for 25 days for evidence of spontaneous recurrent herpatic lesions. Recurrent episodes were enumerated as cumulative recurrences (appearance of lesions) per guinea pig for each group, adjusted for the number of days the recurrences were observed. FIG. 6 shows the number of recurrences in each treatment group for the period of time following administration of the priming dose and immediately before the first boost (day 15 to day 42 post-infection). The data show that administration of the priming dose of gD-DNA vector in the mucosal vaccine group had a rapid therapeutic effect in reducing the number of recurrences of herpatic lesions. T cell responses induced by administration of the priming dose of gD-DNA vector (data not shown) appear to correlate with this rapid and significant therapeutic efficacy observed from day 28 to day 42. In contrast, no effect on the number of recurrences was observed for animals which received the HSV-2 gD subunit vaccine despite the fact that this reference vaccine induced a significant increase in anti-HSV-2 gD serum IgG during this time period (compare FIG. 3A and FIG. 6).

Figure 7:
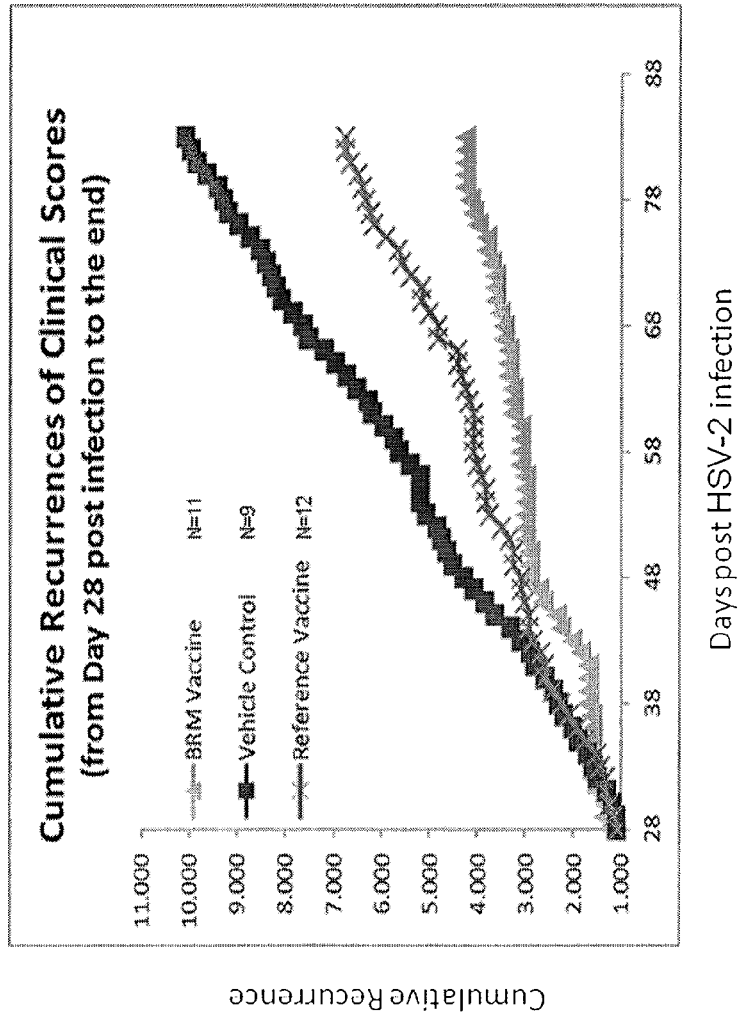
FIG. 7. Cumulative recurrence per animal per group in unvaccinated guinea pigs (vehicle control) or guinea pigs vaccinated either with the mucosal vaccine (BRM vaccine) or an HSV-2 gD subunit vaccine (reference vaccine) from day 28 to day 83 post-infection with HSV-2. Animals were observed for evidence of spontaneous recurrent herpatic lesions and recurrent episodes were enumerated as cumulative recurrences (appearance of lesions) per guinea pig for each group, adjusted for the number of days the recurrences were observed. The table lists the slopes of linear regression for selected periods of days post infection for each treatment group.

FIG. 7 depicts the number of recurrences in each treatment group for the period of time following administration of the priming dose to the end of the study (day 28 to day 83 post-infection). The data indicate that the administration of the mucosal vaccine to pre-infected guinea pigs markedly reduced the number of recurrences of HSV-2 clinical disease as compared to unvaccinated animals and animals receiving the HSV-2 gD subunit vaccine. The Table in FIG. 7 shows that post vaccination the difference between the mucosal vaccine group and the other two treatment groups is highly significant ($P<0.0001$).

In summary, the results of the series of experiments described in this example show that a mucosal vaccine, which comprises both DNA and protein antigen components, induces strong vaginal IgG and IgA antibody responses, reduces vaginal viral shedding, and significantly and rapidly reduces the number of recurrences of herpetic lesions in infected animals. In contrast, a subcutaneously administered HSV-2 gD subunit vaccine comprising alum and MPL adjuvants induces strong, rapid serum IgG antibody responses, but fails to induce significant mucosal antibody responses. The subunit vaccine also does not reduce viral shedding and is less effective in reducing the number of recurrences of herpatic lesions than the mucosal vaccine.

All publications, patents and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

1. Handsfield H H, Stone K M, Wasserheit J N. Prevention agenda for genital herpes. Sex Transm Dis 1999; 26(4): 228-31.
2. Lafferty W E, Coombs R W, Benedetti J, Critchlow C, Corey L. Recurrences after oral and genital herpes simplex virus infection. Influence of site of infection and viral type. N Engl J Med 1987; 316(23):1444-9.
3. Mertz G J, Benedetti J, Ashley R, Selke S A, Corey L. Risk factors for the sexual transmission of genital herpes. Ann Intern Med 1992; 116(3):197-202.
4. Wald A, Corey L, Cone R, Hobson A, Davis G, Zeh J. Frequent genital herpes simplex virus 2 shedding in immunocompetent women. Effect of acyclovir treatment. J Clin Invest 1997; 99(5):1092-7.
5. Straus S, Corey L. Herpes simplex viruses. In: Mandell G L, Douglas R G, Bennett J E, Dolin R, editors. Mandell, Douglas, and Bennett's principles and practice of infectious diseases. Philadelphia [etc.]: Churchill Livingstone; 2000. p. 1556-80.
6. Kimberlin D W. Antiviral therapy for cytomegalovirus infections in pediatric patients. Semin Pediatr Infect Dis 2002; 13(1):22-30.
7. Stamm W E, Handsfield H H, Rompalo A M, Ashley R L, Roberts P L, Corey L. The association between genital ulcer disease and acquisition of HIV infection in homosexual men. JAMA 1988; 260(10): 1429-33.
8. Stanberry L R, Spruance S L, Cunningham A L, Bernstein D I, Mindel A, Sacks S. et al. Glycoprotein-d-adjuvant vaccine to prevent genital herpes. N Engl J Med 2002; 347(21):1652-61.
9. Whitley R J, Kimberlin D W, Roizman B. Herpes simplex viruses. Clin Infect Dis 1998; 26(3):541-53, quiz 554-545.
10. Ashley R L, Dalessio J, Burchett S, Brown Z, Berry S. Mohan K, et al. Herpes simplex virus-2 (HSV-2) type-specific antibody correlates of protection in infants exposed to HSV-2 at birth. J Clin Invest 1992; 90(2):511-4.
11. Dudley K L, Bourne N, Milligan G N. Immune protection against HSV-2 in B-cell-deficient mice. Virology 2000; 270(2):454-63.
12. Mester J C, Milligan G N, Bernstein D I. The immunobiology of herpes simplex virus. In: Stanberry L R, editor. Genital and neonatal herpes. New York: John Wiley and Sons, Ltd.; 1996. p. 49-91.
13. Milligan G N, Bernstein D I. Analysis of herpes simplex virus-specific T cells in the murine female genital tract following genital infection with herpes simplex virus type 2. Virology 1995; 212(2):481-9.
14. Speck P, Simmons A. Precipitous clearance of herpes simplex virus antigens from the peripheral nervous systems of experimentally infected C57BL10 mice. J Gen Virol 1998; 79(Pt 3):561-4.
15. Koelle D M, Posavad C M, Barnum G R, Johnson M L, Frank J M, Corey L. Clearance of HSV-2 from recurrent genital lesions correlates with infiltration of HSV-specific cytotoxic T lymphocytes. J Clin Invest 1998; 101(7): 1500-8.
16. Posavad C M, Koelle D M, Shaughnessy M F, Corey L. Severe genital herpes infections in HIV-infected individuals with impaired herpes simplex virus-specific CD8+ cytotoxic T lymphocyte responses. Proc Natl Acad Sci USA 1997; 94(19): 10289-94.
17. Posavad C M, Koelle D M, Corey L. Tipping the scales of herpes simplex virus reactivation: the important responses are local. Nat Med 1998; 4(4):381-2.
18. Parr M B, Parr E L. Mucosal immunity in the female and male reproductive tracts. In: Ogra P L, Lamm M E, Strober W, McGhee J R, Bienenstock J, editors. Handbook of mucosal immunology. San Diego: Academic Press; 1994. p. 677-89.
19. Parr M B, Parr E L. Mucosal immunity to herpes simplex virus type 2 infection in the mouse vagina is impaired by in vivo depletion of T lymphocytes. J Virol 1998; 72(4): 2677-85.
20. Milligan G N, Bernstein D I, Bourne N. T lymphocytes are required for protection of the vaginal mucosae and sensory ganglia of immune mice against reinfection with herpes simplex virus type 2. J Immunol 1998; 160(12): 6093-100.
21. Kuklin N A, Daheshia M. Chun S, Rouse B T. Role of mucosal immunity in herpes simplex virus infection. J Immunol 1998; 160(12):5998-6003.
22. Gallichan W S, Rosenthal K L. Long-term immunity and protection against herpes simplex virus type 2 in the 23. Neutra M R, Kozlowski P A. Mucosal vaccines: the promise and the challenge. Nat Rev Immunol 2006; 6(2): 148-58.
24. Seder R A, Hill A V. Vaccines against intracellular infections requiring cellular immunity. Nature 2000; 406 (6797):793-8.
25. Robinson H L, Montefiori D C, Johnson R P, Manson K H, Kalish M L, Lifson J D, et al. Neutralizing antibody-independent containment of immunodeficiency virus challenges by DNA priming and recombinant pox virus booster immunizations. Nat Med 1999; 5(5):526-34.
26. Yang K, Whalen B J, Tirabassi R S, Selin L K, Levchenko T S, Torchilin V P, et al. A DNA vaccine prime followed by a liposome-encapsulated protein boost confers enhanced mucosal immune responses and protection. J Immunol 2008; 180(9):6159-67.
27. O'Hagan D T. Recent developments in vaccine delivery systems. Curr Drug Targets Infect Disord 2001; 1(3):273-86.
28. Alving C R, Koulchin V, Glenn G M, Rao M. Liposomes as carriers of peptide antigens: induction of antibodies and cytotoxic T lymphocytes to conjugated and unconjugated peptides. Immunol Rev 1995; 145:5-31.
29. Bourne N, Milligan G N, Schleiss M R. Bernstein D I, Stanberry L R. DNA immunization confers protective immunity on mice challenged intravaginally with herpes simplex virus type 2. Vaccine 1996; 14(13):1230-4.
30. Bernstein D I, Tepe E R, Mester J C, Arnold R L, Stanberry L R, Higgins T. Effects of DNA immunization formulated with bupivacaine in murine and guinea pig models of genital herpes simplex virus infection. Vaccine 1999; 17(15-16):1964-9.
31. Cattamanchi A, Posavad C M, Wald A, Baine Y, Moses J, Higgins T J, et al. Phase I study of a herpes simplex virus type 2 (HSV-2) DNA vaccine administered to healthy, HSV-2 seronegative adults by a needle-free injection system. Clin Vaccine Immunol 2008; 15(11):1638-43.
32. Posavad C M, Remington M, Mueller D E, Zhao L, Magaret A S, Wald A, et al. Detailed characterization of T cell responses to herpes simplex virus-2 in immune seronegative persons. J Immunol 2010; 184(6):3250-9.
33. Pertmer T M, Roberts T R, Haynes J R. Influenza virus nucleoprotein-specific immunoglobulin G subclass and cytokine responses elicited by DNA vaccination are dependent on the route of vector DNA delivery. J Virol 1996; 70(9):6119-25.
34. Feltquate D M, Heaney S, Webster R G, Robinson H L. Different T helper cell types and antibody isotypes generated by saline and gene gun DNA immunization. J Immunol 1997; 158(5):2278-84.
35. Parr M B, Parr E L. The role of gamma interferon in immune resistance to vaginal infection by herpes simplex virus type 2 in mice. Virology 1999; 258(2): 282-94.
36. Milligan G N, Bernstein D I. Interferon-gamma enhances resolution of herpes simplex virus type 2 infection of the murine genital tract. Virology 1997; 229(1): 259-68.
37. Baral R N, Saha A, Chatterjee S K, Foon K A, Krieg A M, Weiner G J, et al. Immunostimulatory CpG oligonucleotides enhance the immune response of anti-idiotype vaccine that mimics carcinoembryonic antigen. Cancer Immunol Immunother 2003; 52(5):317-27.
38. Sandler A D, Chihara H, Kobayashi G, Zhu X, Miller M A, Scott D L, et al. CpG oligonucleotides enhance the tumor antigen-specific immune response of a granulocyte macrophage colony-stimulating factor-based vaccine strategy in neuroblastoma. Cancer Res 2003; 63(2):394-9.
39. Kutzler M A, Weiner D B. DNA vaccines: ready for prime time? Nat Rev Genet. 2008; 9(10):776-88.
40. Lu S. Immunogenicity of DNA vaccines in humans: it takes two to tango. Hum Vaccin 2008; 4(6):449-52.
41. Domingo C, Gadea I, Pardeiro M, Castilla C, Fernandez S, Fernandez-Clua M A, et al. Immunological properties of a DNA plasmid encoding a chimeric protein of herpes simplex virus type 2 glycoprotein B and glycoprotein D. Vaccine 2003; 21(25-26):3565-74.
42. Bridges P A, Taylor K M. The effects of freeze-drying on the stability of liposomes to jet nebulization. J Pharm Pharmacol 2001; 53(3):393-8.
43. Bridges P A, Taylor K M. An investigation of some of the factors influencing the jet nebulisation of liposomes. Int J Pharm 2000; 204(1-2):69-79.
44. Alving C R. Design and selection of vaccine adjuvants: animal models and human trials. Vaccine 2002; 20(Suppl. 3):S56-64.
45. Moynihan J S, Jones D H, Farrar G H, Howard C R. A novel microencapsulated peptide vaccine against hepatitis B. Vaccine 2001; 19(23-24):3292-300.
46. Natuk R J, Cooper D, Guo M, Calderon P, Wright K J, Nasar F, et al. Recombinant vesicular stomatitis virus vectors expressing herpes simplex virus type 2 gD elicit robust CD4+ Th1 immune responses and are protective in mouse and guinea pig models of vaginal challenge. J Virol 2006; 80(9):4447-57.

SEQUENCES

Human codon-optimized HSV-2 gD nucleotide sequence
(SEQ ID NO: 1)
ATGGGACGGCTGACCAGCGGAGTGGGCACAGCCGCCCTGCTGGTCGTGGCTGTGGGCCTGCGCG

TGGTGTGCGCCAAGTACGCCCTGGCCGACCCCAGCCTGAAGATGGCCGACCCCAACCGGTTCCG

CGGCAAGAACCTGCCCGTGCTGGACCAGCTGACCGACCCTCCCGGCGTGAAGCGCGTGTACCAC

ATCCAGCCCAGCCTGGAGGACCCCTTCCAGCCCCCAGCATCCCCATCACCGTGTACTACGCCG

TGCTGGAGCGCGCCTGCCGGAGCGTGCTGCTGCACGCCCCAGCGAGGCCCCCCAGATTGTGCG

CGGAGCCAGCGACGAGGCCCGGAAGCACACCTACAACCTGACCATCGCCTGGTATCGGATGGGC

GACAACTGCGCCATCCCTATTACCGTGATGGAGTACACCGAGTGCCCCTACAACAAGAGCCTGG

GAGTGTGCCCCATCCGGACCCAGCCCCGGTGGAGCTACTACGACAGCTTCAGCGCTGTGAGCGA

| SEQUENCES |
|---|

```
GGACAACCTGGGCTTCCTGATGCACGCCCCTGCCTTCGAGACCGCCGGCACCTACCTGCGGCTG

GTGAAGATCAACGACTGGACCGAGATCACCCAGTTCATCCTGGAGCACCGCGCCAGAGCCAGCT

GCAAATACGCCCTGCCCCTGCGGATCCCCCCTGCCGCCTGCCTGACCAGCAAGGCCTATCAGCA

GGGCGTGACCGTGGACAGCATCGGCATGCTGCCCCGGTTCATCCCCGAGAACCAGCGGACCGCG

GCCCTGTACTCTCTGAAGATCGCCGGCTGGCACGGCCCCAAGCCCCCCTACACCAGCACCCTGC

TGCCCCCCGAGCTGAGCGACACCACCAACGCCACCCAGCCCGAGCTGGTGCCCGAGGACCCCGA

GGATAGCGCCCCGCTGGAGGATCCCGCCGGAACAGTGAGCAGCCAGATCCCCCCCAACTGGCAC

ATCCCTAGCATCCAGGACGTGGCCCCCCACCACGCCCCAGCCGCCCCTAGCAACCCCGGCCTGA

TCATCGGCGCCCTGGCCGGCAGCACCCTGGCCGCCCTGGTGATCGGCGGCATCGCCTTTTGGGT

GCGCAGACGCGCCCAGATGGCCCCCAAGCGGCTGCGGCTGCCCCACATCCGCGACGACGACGCC

CCTCCATCTCACCAGCCCCTGTTCTAG
```

Truncated gD amino acid sequence-amino acids 1-314
(SEQ ID NO: 2)
```
M G R L T S G V G T A A L L V V A V G L R V V C A K Y A L A D P
S L K M A D P N R F R G K N L P V L D Q L T D P P G V K R V Y H
I Q P S L E D P F Q P P S I P I T V Y Y A V L E R A C R S V L L
H A P S E A P Q I V R G A S D E A R K H T Y N L T I A W Y R M G
D N C A I P I T V M E Y T E C P Y N K S L G V C P I R T Q P R W
S Y Y D S F S A V S E D N L G F L M H A P A F E T A G T Y L R L
V K I N D W T E I T Q F I L E H R A R A S C K Y A L P L R I P P
A A C L T S K A Y Q Q G V T V D S I G M L P R F I P E N Q R T V
A L Y S L K I A G W H G P K P P Y T S T L L P P E L S D T T N A
T Q P E L V P E D P E D S A L L E D P A G T V S S Q
```

Full-length gD amino acid sequence
(SEQ ID NO: 3)
```
M G R L T S G V G T A A L L V V A V G L R V V C A K Y A L A D P
S L K M A D P N R F R G K N L P V L D Q L T D P P G V K R V Y H
I Q P S L E D P F Q P P S I P I T V Y Y A V L E R A C R S V L L
H A P S E A P Q I V R G A S D E A R K H T Y N L T I A W Y R M G
D N C A I P I T V M E Y T E C P Y N K S L G V C P I R T Q P R W
S Y Y D S F S A V S E D N L G F L M H A P A F E T A G T Y L R L
V K I N D W T E I T Q F I L E H R A R A S C K Y A L P L R I P P
A A C L T S K A Y Q Q G V T V D S I G M L P R F I P E N Q R T V
A L Y S L K I A G W H G P K P P Y T S T L L P P E L S D T T N A
T Q P E L V P E D P E D S A L L E D P A G T V S S Q I P P N W H
I P S I Q D V A P H H A P A A P S N P G L I I G A L A G S T L A
A L V I G G I A F W V R R R A Q M A P K R L R L P H I R D D D A
P P S H Q P L F
```

Full-length gD amino acid sequence variant #1
(SEQ ID NO: 4)
MGRLTSGVGTAALLWAVGLRWCAKYAIADPSLKMADPNRFRGKNLPVLDQLTDPPGVKRVYH

| SEQUENCES |
|---|
| IQPSLEDPFQPPSIPITVYYAVLEBACRSVLLHAP5EAPQIVRGASDEAKKHTYNLTIAWYRMG |
| DNCAIPITVMEYTECPYNKSLGVCPIRTQPRWSYYDSFSAVSEDNLGFLMHAPAFETAGTYLRL |
| VKINDWTEITQFILEHRARASCKYALPLRIPPAACLTSKAYQQGVTVDSIGMLPRFIPENQRCV |
| ALYSLKIAGWKGPKPPYTSTLLPPELSDTTNATQPELVPEDPSDSALLEDPAGTVSSQIPPNWH |
| IPSIQDVAPHHAPAAPSNPGLIIGALAGSTLAVLVIGGIAFW/RRRAQMAPKRLRLPHIRDDDA |
| PPSHQPLFY |
| Full-length gD amino acid sequence variant #2 (SEQ ID NO: 5) |
| MGRLTSGVGTAALLWAVGLRWCAKYALADPSLKMADPNRFRGKNLPVLDRLTDPPGVKRVYH |
| IQPSLEDPFQPPSIPITVYYAVLERACRSVLLHAPSEAPQIVRGASDEARKHTYNLTIAWYRMG |
| DNCAIPITVMEYTECPYNKSLGVCPIRTQPRWSYYDSFSAVSEDNLGFLMHAPAFETAGTYLRL |
| VKINDWTEITQFILEHRARASCKYALPLRIPPAACLTSKAYQQGVTVDSIGMLPRFIPENQRTV |
| ALYSLKIAGWHGPKPPYISTLLPPELSDTTNATQPELVPEDPEDSALLEDPAGTVSSQIPPNWH |
| IPSIQDVAPHHAPAAPSN GLIIGALAGSTLAVLVIGGIAFWVRRRAQMAPKRLRLPHIRDDDA |
| PPSHQPLFY |

Full-length gD amino acid
sequence variant #3 (SEQ ID NO: 6)
MGRLTSGVGTAALLVVAVGLRVVCAKYALADPSLKMADPNRFRGKNLPVL

DQLTDPPGVKRVYH IQPSLEDPFQPPSIPITVYYALVERACRSVLLHA

PSEAPQIVRGASDEARKHTYNLTIAWYRMG DNCAIPITVMEYTECPYNK

SLGVCPIRTQPRWSYYDSFSAVSEDNLGFLIHAPAFETAGTYLRLVKIND

WTEITQFILEHRARASCKYALPLRIPPAACLTSKAYQQGVTVDSIGMLPR

FIPENQRTVALYSLKIAGWHGPKPPYTSTLLPPELSDTTNATQPELVPED

PEDSALLEDPAGTVSSQIPPNWHIPSIQDVAPHHAPAAPSNPGLIIGALA

GSTLAVLVIGGIAFWVRRRAQMAPKRLRLPHIRDDDAPPSHQPLFY

Full-length gD amino acid
sequence variant #4 (SEQ ID NO: 7)
MGRLTSGVGTAALLVVAVGLRVVCAKYALADPSLKMADPNRFRGKNLPVL

DQLTDPPGVKRVYHIQPSLEDPFQPPSIPITVYYAVLERACRSVLLHAPS

EAPQIVRGASDEARKHTYNLTIAWYRMGDNCAIPITVMEYTECPYNKSLG

VCPIRTQPRWSYYDSFSAVSEDNLGFLMHAPAFETAGTYLRLVKINDWTE

ITQFILEHRARASCKYALPLRIPPAACLTSKAYQQGVTVDSIGMLPRFIP

ENQRTVALYSLKIAGWHGPKPPYTSTLLPPELSDTTNATQPELVPEDPED

SALLEDPAGTVSSQIPPNWHIPSIQDVAPHHAPAAPSNPGLIIGALAGST

LAVLVIGGIAFWVRRRAQMAPKRLRLPHIRDDDAPPSHQPLFY

The invention claimed is:

1. A method for treating a herpes simplex virus type 2 (HSV-2) infection in a mammal, wherein the method comprises the steps of:
    (a) administering to the mammal a priming preparation comprising a vector encoding an HSV-2 antigen under the control of a promoter, wherein the vector encodes a full-length gD sequence comprising a sequence of SEQ ID NO: 1;

(b) after step (a), administering to the mammal a first boosting preparation comprising the HSV-2 antigen encapsulated in liposomes; and (c) after step (b), administering to the mammal a second boosting preparation comprising the vector encoding the HSV-2 antigen and the liposomal-encapsulated HSV-2 antigen, wherein the vector is administered intramuscularly and the liposomal-encapsulated antigen is administered intranasally.

2. The method of claim 1, wherein the priming preparation is administered in one or two administrations.

3. The method of claim 1, wherein the first boosting preparation is administered to the mammal about 2 to 4 weeks after the priming preparation.

4. The method of claim 1, wherein the first boosting preparation is administered to the mammal about 7 to 18 days after the priming preparation.

5. The method of claim 4, wherein the first boosting preparation is administered to the mammal about 10 to 16 days after the priming preparation.

6. The method of claim 1, wherein the second boosting preparation is administered to the mammal about 2 to 4 weeks after the first boosting preparation.

7. The method of claim 1, wherein the second boosting preparation is administered to the mammal about 7 to 18 days after the first boosting preparation.

8. The method of claim 7, wherein the second boosting preparation is administered to the mammal about 10 to 16 days after the first boosting preparation.

9. The method of claim 1, further comprising administering to the mammal a combination of the vector encoding the HSV-2 antigen and the HSV-2 antigen encapsulated in liposomes at the sign of recurrence of herpetic lesions.

10. The method of claim 1, wherein one or more symptoms of HSV-2 infection is ameliorated in the mammal following administration of the second boosting preparation.

11. The method of claim 10, wherein the recurrence of herpetic lesions is reduced in the mammal as compared to an untreated mammal or a mammal vaccinated with a non-mucosal vaccine.

12. The method of claim 10, wherein viral shedding is reduced in the mammal as compared to an untreated mammal or a mammal vaccinated with a non-mucosal vaccine.

13. The method of claim 1, wherein antigen-specific IgA and IgG is increased in the vaginal secretions of the mammal as compared to an untreated mammal or a mammal vaccinated with a non-mucosal vaccine.

14. The method of any one of claims 11 to 13, wherein the non-mucosal vaccine comprises a truncated HSV-2 glycoprotein D (gD) formulated for subcutaneous administration.

15. The method of claim 1, wherein the promoter is a cytomegalovirus promoter.

16. The method of claim 15, wherein the cytomegalovirus promoter is an immediate early promoter.

17. The method of claim 1, wherein the HSV-2 antigen encoded by the vector is codon-optimized for expression in mammalian cells.

18. The method of claim 1, wherein the HSV-2 antigen encoded by the vector is codon-optimized for expression in human cells.

19. The method of claim 1, wherein the liposomal-encapsulated antigen in the first and second boosting preparations is an extracellular domain of gD.

20. The method of claim 19, wherein the antigen comprises a sequence of SEQ ID NO: 2.

21. The method of claim 1, wherein the liposomes are anionic liposomes.

22. The method of claim 21, wherein the liposomes have an average diameter of about 0.5-5 μm.

23. The method of claim 1, wherein the mammal is human.

24. A method for treating a herpes simplex virus type 2 (HSV-2) infection in a mammal, wherein the method comprises the steps of:
(a) administering to the mammal a priming preparation comprising a vector encoding an HSV-2 antigen under the control of a promoter, wherein the vector encodes a full-length gD sequence comprising a sequence of SEQ ID NO: 1;
(b) after step (a), administering to the mammal a first boosting preparation comprising the HSV-2 antigen encapsulated in liposomes, wherein the liposomal-encapsulated antigen is an extracellular domain of gD comprising a sequence of SEQ ID NO: 2; and
(c) after step (b), administering to the mammal a second boosting preparation comprising the vector encoding the HSV-2 antigen and the liposomal-encapsulated HSV-2 antigen,
wherein the vector is administered intramuscularly and the liposomal-encapsulated antigen is administered intranasally.

* * * * *